US008580313B2

(12) United States Patent
Mapelli et al.

(10) Patent No.: US 8,580,313 B2
(45) Date of Patent: Nov. 12, 2013

(54) FEXOFENADINE MICROCAPSULES AND COMPOSITIONS CONTAINING THEM

(75) Inventors: Luigi Mapelli, Milan (IT); Flavio Fabiani, Ronco Briantino (IT); Luigi Boltri, Agrate Brianza (IT); Paolo Gatti, Sesto San Giovanni (IT); Mauro Serratoni, Cuggiono (IT); Roberto Cassanmagnago, Macherio (IT)

(73) Assignee: Aptalis Pharma Limited, Wicklow (IE)

( * ) Notice: Subject to any disclaimer, the term of this patent is extended or adjusted under 35 U.S.C. 154(b) by 0 days.

(21) Appl. No.: 12/959,113

(22) Filed: Dec. 2, 2010

(65) Prior Publication Data

US 2011/0250281 A1  Oct. 13, 2011

Related U.S. Application Data

(60) Provisional application No. 61/265,823, filed on Dec. 2, 2009, provisional application No. 61/354,575, filed on Jun. 14, 2010.

(51) Int. Cl.
*A61K 9/16* (2006.01)
*A61K 9/50* (2006.01)
*A61K 31/445* (2006.01)
*A61P 11/02* (2006.01)
*A61P 29/00* (2006.01)
*B01J 13/22* (2006.01)

(52) U.S. Cl.
USPC ........... 424/495; 424/490; 424/494; 424/497; 514/317

(58) Field of Classification Search
None
See application file for complete search history.

(56) References Cited

U.S. PATENT DOCUMENTS

| 3,184,386 A | 5/1965 | Stephenson |
| 3,558,768 A | 1/1971 | Klippel |
| 3,885,026 A | 5/1975 | Heinemann et al. |
| 4,078,051 A | 3/1978 | Pomot et al. |
| 4,138,475 A | 2/1979 | McAinsh et al. |
| 4,248,857 A | 2/1981 | DeNeale et al. |
| 4,292,017 A | 9/1981 | Doepel |
| 4,305,502 A | 12/1981 | Gregory et al. |
| 4,369,172 A | 1/1983 | Schor et al. |
| 4,371,516 A | 2/1983 | Gregory et al. |
| 4,389,330 A | 6/1983 | Tice et al. |
| 4,389,393 A | 6/1983 | Schor et al. |
| 4,542,042 A | 9/1985 | Samejima et al. |
| 4,556,678 A | 12/1985 | Hsiao |

(Continued)

FOREIGN PATENT DOCUMENTS

| EP | 0052492 B1 | 2/1984 |
| EP | 0166440 A2 | 1/1986 |

(Continued)

OTHER PUBLICATIONS

GOOGLE translation specification of WO 2000051568; Aug. 9, 2000; 4 pages.*

(Continued)

*Primary Examiner* — Ernst Arnold
(74) *Attorney, Agent, or Firm* — Cooley LLP

(57) ABSTRACT

The present invention provides a pharmaceutical composition comprising taste-masked immediate release microcapsules which comprise fexofenadine and a water-insoluble polymer coating. These microcapsules and the pharmaceutical compositions comprising them have suitable drug content and desirable pharmaceutical properties, including a quick dissolution rate of fexofenadine combined with a taste masking effect.

33 Claims, 17 Drawing Sheets

(56) References Cited

U.S. PATENT DOCUMENTS

| | | |
|---|---|---|
| 4,587,118 A | 5/1986 | Hsiao |
| 4,628,098 A | 12/1986 | Nohara et al. |
| 4,661,647 A | 4/1987 | Serpelloni et al. |
| 4,670,459 A | 6/1987 | Sjoerdsma |
| 4,689,333 A | 8/1987 | Nohara et al. |
| 4,698,101 A | 10/1987 | Koivurinta |
| 4,708,867 A | 11/1987 | Hsiao |
| 4,713,248 A | 12/1987 | Kjornaes et al. |
| 4,716,041 A | 12/1987 | Kjornaes et al. |
| 4,728,512 A | 3/1988 | Mehta et al. |
| 4,743,248 A | 5/1988 | Bartoo et al. |
| 4,752,470 A | 6/1988 | Mehta |
| 4,757,090 A | 7/1988 | Salpekar et al. |
| 4,760,093 A | 7/1988 | Blank et al. |
| 4,780,318 A | 10/1988 | Appelgren et al. |
| 4,786,508 A | 11/1988 | Ghebre-Sellassie et al. |
| 4,800,087 A | 1/1989 | Mehta |
| 4,803,213 A | 2/1989 | Iida et al. |
| 4,824,675 A | 4/1989 | Wong et al. |
| 4,832,880 A | 5/1989 | Staniforth |
| 4,840,799 A | 6/1989 | Appelgren et al. |
| 4,851,226 A | 7/1989 | Julian et al. |
| 4,851,229 A | 7/1989 | Magruder et al. |
| 4,863,742 A | 9/1989 | Panoz et al. |
| 4,871,549 A | 10/1989 | Ueda et al. |
| 4,874,613 A | 10/1989 | Hsiao |
| 4,886,669 A | 12/1989 | Ventouras |
| 4,892,741 A | 1/1990 | Ohm et al. |
| 4,894,240 A | 1/1990 | Geoghegan et al. |
| 4,898,737 A | 2/1990 | Panoz et al. |
| 4,915,949 A | 4/1990 | Wong et al. |
| 4,938,968 A | 7/1990 | Mehta |
| 4,946,684 A | 8/1990 | Blank et al. |
| 4,957,745 A | 9/1990 | Jonsson et al. |
| 4,968,508 A | 11/1990 | Oren et al. |
| 4,971,805 A | 11/1990 | Kitanishi et al. |
| 4,983,401 A | 1/1991 | Eichel et al. |
| 5,006,345 A | 4/1991 | Lang |
| 5,011,692 A | 4/1991 | Fujioka et al. |
| 5,013,557 A | 5/1991 | Tai |
| 5,013,743 A | 5/1991 | Iwahi et al. |
| 5,017,122 A | 5/1991 | Staniforth |
| 5,017,381 A | 5/1991 | Maruyama et al. |
| 5,026,559 A | 6/1991 | Eichel et al. |
| 5,026,560 A | 6/1991 | Makino et al. |
| 5,039,540 A | 8/1991 | Ecanow |
| 5,045,321 A | 9/1991 | Makino et al. |
| 5,073,374 A | 12/1991 | McCarty |
| 5,075,114 A | 12/1991 | Roche |
| 5,079,018 A | 1/1992 | Ecanow |
| 5,082,669 A | 1/1992 | Shirai et al. |
| 5,084,278 A | 1/1992 | Mehta |
| 5,093,132 A | 3/1992 | Makino et al. |
| 5,104,648 A | 4/1992 | Denton et al. |
| 5,112,616 A | 5/1992 | McCarty |
| 5,133,974 A | 7/1992 | Paradissis et al. |
| 5,137,733 A | 8/1992 | Noda et al. |
| 5,149,542 A | 9/1992 | Valducci |
| 5,160,680 A | 11/1992 | Serpelloni et al. |
| 5,169,640 A | 12/1992 | France et al. |
| 5,178,878 A | 1/1993 | Wehling et al. |
| 5,204,121 A | 4/1993 | Bucheler et al. |
| 5,211,957 A | 5/1993 | Hagemann et al. |
| 5,213,808 A | 5/1993 | Bar-Shalom et al. |
| 5,229,131 A | 7/1993 | Amidon et al. |
| 5,229,135 A | 7/1993 | Philippon et al. |
| 5,238,686 A | 8/1993 | Eichel et al. |
| 5,252,337 A | 10/1993 | Powell |
| 5,256,699 A | 10/1993 | Murphy et al. |
| 5,260,068 A | 11/1993 | Chen |
| 5,260,069 A | 11/1993 | Chen |
| 5,275,827 A | 1/1994 | Spinelli et al. |
| 5,376,384 A | 12/1994 | Eichel et al. |
| 5,409,711 A | 4/1995 | Mapelli et al. |
| 5,433,959 A | 7/1995 | Makino et al. |
| 5,439,689 A | 8/1995 | Hendrickson et al. |
| 5,445,829 A | 8/1995 | Paradissis et al. |
| 5,464,632 A | 11/1995 | Cousin et al. |
| 5,466,464 A | 11/1995 | Masaki et al. |
| 5,470,584 A | 11/1995 | Hendrickson et al. |
| 5,472,708 A | 12/1995 | Chen |
| 5,478,573 A | 12/1995 | Eichel et al. |
| 5,489,436 A | 2/1996 | Hoy et al. |
| 5,501,861 A | 3/1996 | Makino et al. |
| 5,506,345 A | 4/1996 | Riley et al. |
| 5,508,040 A | 4/1996 | Chen |
| 5,529,790 A | 6/1996 | Eichel et al. |
| 5,536,507 A | 7/1996 | Abramowitz et al. |
| 5,567,441 A | 10/1996 | Chen |
| 5,576,014 A | 11/1996 | Mizumoto et al. |
| 5,609,883 A | 3/1997 | Valentine et al. |
| 5,612,059 A | 3/1997 | Cardinal et al. |
| 5,616,345 A | 4/1997 | Geoghegan et al. |
| 5,629,017 A | 5/1997 | Pozzi et al. |
| 5,639,475 A | 6/1997 | Bettman et al. |
| 5,643,630 A | 7/1997 | Hinzpeter et al. |
| 5,700,492 A | 12/1997 | Morimoto et al. |
| 5,720,974 A | 2/1998 | Makino et al. |
| 5,738,875 A | 4/1998 | Yarwood et al. |
| 5,747,068 A | 5/1998 | Mendizabal |
| 5,762,961 A | 6/1998 | Roser et al. |
| 5,788,987 A | 8/1998 | Busetti et al. |
| 5,807,577 A | 9/1998 | Ouali |
| 5,837,284 A | 11/1998 | Mehta et al. |
| 5,837,285 A | 11/1998 | Nakamichi et al. |
| 5,837,379 A | 11/1998 | Chen et al. |
| 5,840,329 A | 11/1998 | Bai |
| 5,876,759 A | 3/1999 | Gowan, Jr. |
| 5,891,474 A | 4/1999 | Busetti et al. |
| 5,900,252 A | 5/1999 | Calanchi et al. |
| 5,908,638 A | 6/1999 | Huber et al. |
| 5,968,554 A | 10/1999 | Beiman et al. |
| 6,024,981 A | 2/2000 | Khankari et al. |
| 6,024,982 A | 2/2000 | Oshlack et al. |
| 6,033,687 A | 3/2000 | Heinicke et al. |
| 6,039,979 A | 3/2000 | Gendrot et al. |
| 6,096,340 A | 8/2000 | Chen et al. |
| 6,099,859 A | 8/2000 | Cheng et al. |
| 6,099,863 A | 8/2000 | Gilis et al. |
| 6,099,865 A | 8/2000 | Augello et al. |
| 6,103,263 A | 8/2000 | Lee et al. |
| 6,106,861 A | 8/2000 | Chauveau et al. |
| 6,106,862 A | 8/2000 | Chen et al. |
| 6,123,962 A | 9/2000 | Makino et al. |
| 6,129,933 A | 10/2000 | Oshlack et al. |
| 6,136,345 A | 10/2000 | Grimmett et al. |
| 6,139,865 A | 10/2000 | Friend et al. |
| 6,139,877 A | 10/2000 | Debregeas et al. |
| 6,153,220 A | 11/2000 | Cumming et al. |
| 6,162,463 A | 12/2000 | Lippa |
| 6,169,105 B1 | 1/2001 | Wong et al. |
| 6,183,776 B1 | 2/2001 | Depui et al. |
| 6,190,692 B1 | 2/2001 | Busetti et al. |
| 6,221,392 B1 | 4/2001 | Khankari et al. |
| 6,221,402 B1 | 4/2001 | Itoh et al. |
| 6,228,398 B1 | 5/2001 | Devane et al. |
| 6,269,615 B1 | 8/2001 | Amborn et al. |
| 6,287,599 B1 | 9/2001 | Burnside et al. |
| 6,316,029 B1 | 11/2001 | Jain et al. |
| 6,328,994 B1 | 12/2001 | Shimizu et al. |
| 6,344,215 B1 | 2/2002 | Bettman et al. |
| 6,350,470 B1 | 2/2002 | Pather et al. |
| 6,350,471 B1 | 2/2002 | Seth |
| 6,365,182 B1 | 4/2002 | Khankari et al. |
| 6,368,625 B1 | 4/2002 | Siebert et al. |
| 6,368,628 B1 | 4/2002 | Seth |
| 6,372,253 B1 | 4/2002 | Daggy et al. |
| 6,391,335 B1 | 5/2002 | Pather et al. |
| 6,413,549 B2 | 7/2002 | Green et al. |
| 6,420,473 B1 | 7/2002 | Chittamuru et al. |
| 6,432,534 B1 | 8/2002 | Hayakawa et al. |
| 6,465,009 B1 | 10/2002 | Liu et al. |
| 6,465,010 B1 | 10/2002 | Lagoviyer et al. |
| 6,495,160 B2 | 12/2002 | Esposito et al. |

(56) References Cited

U.S. PATENT DOCUMENTS

| | | |
|---|---|---|
| 6,500,454 B1 | 12/2002 | Percel et al. |
| 6,509,034 B1 | 1/2003 | Calanchi et al. |
| 6,509,036 B2 | 1/2003 | Pather et al. |
| 6,531,152 B1 | 3/2003 | Lerner et al. |
| 6,551,617 B1 | 4/2003 | Corbo et al. |
| 6,569,463 B2* | 5/2003 | Patel et al. ............... 424/497 |
| 6,579,535 B2 | 6/2003 | Valentine et al. |
| 6,596,311 B1 | 7/2003 | Dobetti |
| 6,602,521 B1 | 8/2003 | Ting et al. |
| 6,627,223 B2 | 9/2003 | Percel et al. |
| 6,641,838 B2 | 11/2003 | Pather et al. |
| 6,660,382 B2 | 12/2003 | Nouri et al. |
| 6,663,888 B2 | 12/2003 | Percel et al. |
| 6,663,893 B2 | 12/2003 | Corbo et al. |
| 6,723,348 B2* | 4/2004 | Faham et al. ............ 424/490 |
| 6,740,341 B1 | 5/2004 | Holt et al. |
| 6,897,205 B2 | 5/2005 | Beckert et al. |
| 7,048,945 B2 | 5/2006 | Percel et al. |
| 2001/0007680 A1 | 7/2001 | Kolter et al. |
| 2001/0014340 A1 | 8/2001 | Ohta et al. |
| 2001/0046964 A1 | 11/2001 | Percel et al. |
| 2002/0054907 A1 | 5/2002 | Devane et al. |
| 2002/0077348 A1 | 6/2002 | Dean et al. |
| 2002/0142034 A1 | 10/2002 | Shimizu et al. |
| 2002/0187190 A1 | 12/2002 | Cade et al. |
| 2003/0064108 A1 | 4/2003 | Lukas et al. |
| 2003/0096791 A1 | 5/2003 | Gupte et al. |
| 2003/0113374 A1 | 6/2003 | Percel et al. |
| 2003/0134884 A1 | 7/2003 | Hazama et al. |
| 2003/0157173 A1 | 8/2003 | Percel et al. |
| 2003/0161888 A1 | 8/2003 | Fernandez et al. |
| 2003/0215500 A1 | 11/2003 | Ohta et al. |
| 2004/0047906 A1 | 3/2004 | Percel et al. |
| 2004/0121010 A1 | 6/2004 | Hirsh et al. |
| 2004/0122106 A1 | 6/2004 | Ohta et al. |
| 2004/0126427 A1 | 7/2004 | Venkatesh et al. |
| 2004/0131682 A1 | 7/2004 | Percel et al. |
| 2004/0137156 A1 | 7/2004 | Lee et al. |
| 2004/0242536 A1 | 12/2004 | Khoo et al. |
| 2005/0025824 A1 | 2/2005 | Percel et al. |
| 2005/0118268 A1 | 6/2005 | Percel et al. |
| 2005/0152974 A1 | 7/2005 | Boehm et al. |
| 2005/0232988 A1 | 10/2005 | Venkatesh et al. |
| 2005/0269722 A1 | 12/2005 | De Luigi Bruschi et al. |
| 2005/0288328 A1* | 12/2005 | Weiner et al. ............... 514/317 |
| 2006/0024361 A1* | 2/2006 | Odidi et al. ............... 424/464 |
| 2006/0057199 A1 | 3/2006 | Venkatesh et al. |
| 2006/0078614 A1 | 4/2006 | Venkatesh et al. |
| 2006/0105038 A1 | 5/2006 | Lai et al. |
| 2006/0105039 A1 | 5/2006 | Lai et al. |
| 2006/0246134 A1 | 11/2006 | Venkatesh |
| 2006/0269607 A1 | 11/2006 | Percel et al. |
| 2007/0048373 A1 | 3/2007 | Chastain et al. |
| 2009/0263480 A1 | 10/2009 | Lai et al. |

FOREIGN PATENT DOCUMENTS

| | | | |
|---|---|---|---|
| EP | 0239361 | A1 | 9/1987 |
| EP | 0349103 | A1 | 1/1990 |
| EP | 0357369 | A2 | 3/1990 |
| EP | 0391518 | A2 | 10/1990 |
| EP | 0431877 | A1 | 6/1991 |
| EP | 0453001 | A1 | 10/1991 |
| EP | 0516345 | A1 | 12/1992 |
| EP | 0538034 | A1 | 4/1993 |
| EP | 0553777 | A2 | 8/1993 |
| EP | 0650826 | A1 | 5/1995 |
| EP | 0721777 | A2 | 7/1996 |
| EP | 0815931 | A1 | 1/1998 |
| EP | 0294493 | A1 | 12/1998 |
| EP | 0914818 | A1 | 5/1999 |
| EP | 0914823 | A1 | 5/1999 |
| EP | 1010423 | A2 | 6/2000 |
| EP | 0582396 | B1 | 1/2001 |
| EP | 1070497 | A1 | 1/2001 |
| EP | 1072257 | A1 | 1/2001 |
| EP | 1157690 | A1 | 11/2001 |
| EP | 1219291 | A1 | 7/2002 |
| EP | 1156786 | B1 | 3/2003 |
| EP | 1366759 | A1 | 12/2003 |
| EP | 0914823 | B1 | 12/2004 |
| EP | 1491184 | A1 | 12/2004 |
| EP | 2319498 | A1 | 5/2011 |
| FR | 2679451 | A1 | 1/1993 |
| FR | 2766089 | A1 | 1/1999 |
| FR | 2778848 | A1 | 11/1999 |
| GB | 2053787 | A | 2/1981 |
| GB | 8824392.8 | | 9/1989 |
| GB | 2224207 | A | 5/1990 |
| JP | 41-11273 | B | 6/1966 |
| JP | 49-69819 | | 7/1974 |
| JP | 55-129224 | A | 10/1980 |
| JP | 56-014098 | A | 10/1981 |
| JP | 61-143316 | A | 7/1986 |
| JP | 62-50445 | B2 | 10/1987 |
| JP | 62-242616 | A | 10/1987 |
| JP | 62-246513 | A | 10/1987 |
| JP | 62-252723 | A | 11/1987 |
| JP | 63-162619 | A | 7/1988 |
| JP | 63-270624 | A | 11/1988 |
| JP | 1-503385 | A | 11/1989 |
| JP | 1-313420 | A | 12/1989 |
| JP | 2-500747 | A | 3/1990 |
| JP | 2-164824 | A | 6/1990 |
| JP | 2-172918 | A | 7/1990 |
| JP | 2-289512 | A | 11/1990 |
| JP | 3-240724 | A | 10/1991 |
| JP | 4-224517 | A | 8/1992 |
| JP | 5-271054 | A | 10/1993 |
| JP | 5-310558 | A | 11/1993 |
| JP | 6-53658 | B2 | 7/1994 |
| JP | 6-321790 | A | 11/1994 |
| JP | 7-69889 | A | 3/1995 |
| JP | 7-124231 | A | 5/1995 |
| JP | 8-503482 | A | 4/1996 |
| JP | 8-175978 | A | 7/1996 |
| NZ | 550608 | A | 11/2005 |
| NZ | 554346 | A | 5/2006 |
| WO | WO 88/08703 | A1 | 11/1988 |
| WO | WO 88/08704 | A2 | 11/1988 |
| WO | WO 92/10173 | A1 | 6/1992 |
| WO | WO 93/00097 | A1 | 1/1993 |
| WO | WO 93/12769 | A1 | 7/1993 |
| WO | WO 93/13758 | A1 | 7/1993 |
| WO | WO 93/15724 | A1 | 8/1993 |
| WO | WO 94/08576 | A1 | 4/1994 |
| WO | WO 94/12180 | A1 | 6/1994 |
| WO | WO 97/41878 | A1 | 11/1997 |
| WO | WO 97/47287 | A1 | 12/1997 |
| WO | WO 99/04763 | A1 | 2/1999 |
| WO | WO 00/25752 | A1 | 5/2000 |
| WO | WO 00/33821 | A1 | 6/2000 |
| WO | WO 00/42998 | A1 | 7/2000 |
| WO | 00/51568 | | 9/2000 |
| WO | WO 00/51568 | A1 | 9/2000 |
| WO | WO 00/59486 | A2 | 10/2000 |
| WO | WO 01/13898 | A2 | 3/2001 |
| WO | WO 01/72285 | A1 | 10/2001 |
| WO | WO 01/80829 | A2 | 11/2001 |
| WO | WO 02/13794 | A1 | 2/2002 |
| WO | WO 02/43704 | A1 | 6/2002 |
| WO | WO 02/057475 | A1 | 7/2002 |
| WO | WO 02/085336 | A1 | 10/2002 |
| WO | WO 03/013492 | A1 | 2/2003 |
| WO | WO 03/039520 | A1 | 3/2003 |
| WO | WO 03/026613 | A1 | 4/2003 |
| WO | WO 03/041683 | A2 | 5/2003 |
| WO | WO 03/043661 | A1 | 5/2003 |
| WO | WO 03/047552 | A2 | 6/2003 |
| WO | WO 2004/009058 | A1 | 1/2004 |
| WO | WO 2004/022037 | A1 | 3/2004 |

(56) References Cited

FOREIGN PATENT DOCUMENTS

| WO | WO 2004/087111 A1 | 10/2004 |
| WO | WO 2005/097064 A2 | 10/2005 |
| WO | WO 2005/105049 A2 | 11/2005 |

OTHER PUBLICATIONS

GOOGLE translation claims of WO 2000051568; Aug. 9, 2000; 1 page.*
"Low Substituted Hydroxypropylcellulose," Official Monographs for Part II, 2001, NRF, JP XIV, pp. 942-943.
Albrecht, "International Search Report," 6 pages, from International Patent Appl. No. PCT/US02/31535, European Patent Office (Feb. 3, 2003).
Anwar et al., "Chronotherapeutics for Cardiovascular Disease," Drugs 55(5):631-643 (1998).
Bauer et al., Pharmarzeutische Technologie, 5th Edition, 1997, Govi Verlag Frankfurt, pp. 164-166.
Berigan, "Atomoxetine Used Adjunctively With Selective Serotonin Reuptake Inhibitors to Treat Depression," Prim. Care. Companion J. Clin. Psychiatry 6(2):93-94 (2004).
Bodmeier et al., "Theophylline Tablets Coated with Aqueous Latexes Containing Dispersed Pore Formers," J. Pharm. Sci. 79(10):925-928 (1990).
Database WPI, Section Ch, Week 198748, Derwent Publications, Ltd., London, GB; AN 1987-338131, XP002156870.
Fell, Letter to the Editor, J. Pharm. Pharmacol. 1968, vol. 20, pp. 657-658.
FMC Corporation Product Specification for Avicel PH, 2005.
Foreign non-patent publication from Japanese textbook, 1989, Hirokawa Publishing Co.
Fubara, "International Preliminary Examination Report," 3 pages, from International Patent Appl. No. PCT/US02/31535, European Patent Office (Jun. 19, 2003).
Gordon et al., "Effect of the Mode of Super Disintegrant Incoproration on Dissolution in Wet Granulated Tables," J. Pharm. Sci. 82:220-226 (1993).
Gorman et al., An Evaluation of Croscarmellose as a Tablet Disintegrant in Direct Compression Systems, Drug. Dev. Ind. Pharm. 1982; vol. 8, pp. 397-410.
Handbook (Binran) of Granule, vol. 1, Ohmsha Ltd., p. 434 & 438 (May 3, 1975).
Ishino et al., "Design and Preparation of Pulsatile Release Tablet as a New Oral Drug Delivery System," Chem. Pharm. Bull. 40(11):3036-3041 (1992).
Kaneto et al., 2000, Latest Pharmacy, Hirokawa Publishing Co., 1 Edition.
Kawashima, "Low-Substituted Hydroxypropylcellulose as a Sustained-Drug Release Matrix Base or Disintegrant Depending on Its Particle Size and Loading in Formulation," Pharm. Res. 1993, vol. 10(3), pp. 351-355.
Kornblum, "A New Tablet Disintegrating Agent," J. Pharm. Sci., Jan. 1973, vol. 62(1), pp. 43-49.
Kratochvil et al., "Atomoxetine: a selective noradrenaline reuptake inhibitor for the treatment of attention-deficit/hyperactivity disorder," Expert Opin. Pharmacother. 4(7):1165-1174 (2003).
McKenna et al., "Effect of particle size on the compaction mechanism and tensile strength of tablets," J. Pharm. Pharmacol. Jun. 1982, vol. 34(6), pp. 347-351.
McKetta et al., "Table of Contents," Encyclopedia of Chemical Processing and Design (1989).
McKetta et al., Encyclopedia of Chemical Processing and Design, "Organic Phase Separation Conservation," p. 167 (1989).
Mitsuo et al., Pharmaceutics Manual, 1989, Pharmaceutics Manual, Nanzando Co. Ltd.
Nwokole et al., "Tolerance during 29 days of conventional dosing with cimetidine, mizatidine, famotidine or ranitidine," Aliment. Pharmacol. Ther. 4(Suppl. 1):29-45 (1990) Abstract only.
Oh, "International Preliminary Report on Patentability," 5 pages, from International Appl. No. PCT/US2005/037084, United States Patent and Trademark Office, Alexandria, Virginia, USA (mailed Aug. 24, 2007).
Ohira et al., "Effects of Various Histamine $H_2$ -12-Receptor Antagonists on Gastrointestinal Motility and Gastric Emptying," J. Smooth Muscle Res. 29:131-142 (1993).
Pharmaceutical Excipients. London: Pharmaceutical Press. Electronic Version, 2006, Mannitol.
Pharmaceutical Excipients. London: Pharmaceutical Press. Electronic Version, 2006, Lactose Monohydrate.
Pharmaceutical Excipients. London: Pharmaceutical Press. Electronic Version, 2006, Croscarmellose sodium.
Rankin, "International Search Report," 6 pages, PCT International Application No. PCT/US02/39238, European Patent Office (May 8, 2003).
Rudnic et al., "Some Effects of Relatively Low Levels of Eight Tablet Disintegrants on a Direct Compression System," Drug. Dev. Ind. Pharm. 1981, vol. 7(3), pp. 347-358.
Rudnic et al., "Studies of the Utility of Cross Linked Polyvinlpolypyrrolidine as a Tablet Disintegrant," Drug Development and Industrial Pharmacy, 1980, vol. 6, No. 3, pp. 291-309.
Sato et al., "Anticonvulsant effects of tigabine, a new antiepileptic drug: the profile of action in the rat kindling model of epilepsy," Epilepsia 37(Supp. 3):110-111 (1996).
Schifferer, "International Search Report," 4 pages, from International Appl. No. PCT/US2005/037084, European Patent Office, Rijswijk, The Netherlands (mailed Jun. 1, 2006).
Schifferer, "Written Opinion of the International Search Authority," 6 pages, from International Appl. No. PCT/US2005/037084, European Patent Office, Munich, Germany (mailed Jun. 1, 2006).
Shangraw et al., "A new era of tablet disintegrants," Pharm. Technol. 1980, vol. 4(10), pp. 49-57.
Simpson and Jarvis, "Fexofenadine. A Review of its Use in the Management of Seasonal Allergic Rhinitis and Chronic Idiopathic Urticaria," Drugs 59(2):301-321 (2000).
Tirkkonen and Paronen, "Enhancement of drug release from ethylcellulose microcapsules using solid sodium chloride in the wall," Int. J. Pharmaceutics 88:39-51 (1992).
Trottier and Wood, 2005, "Particle Size Measurement," Kirk-Othmer Encyclopedia of Chemical Technology (Extract of 1. Introduction; 2. Data Representation; 4. Measurement Methods; 8. Selection of Equipment).
Ueki et al., "Nizatidine Comparably Enhances Postprandial Gastric Motility to Existing Gastroprokinetics in Dogs," Jpn. Pharmacol. Ther. 28(11):925-930 (2000).
Uhl, "International Search Report," 5 pages, International Patent Appl. No. PCT/US2006/016538, European Patent Office (Feb. 27, 2007).
Uhl, "Written Opinion of the International Searching Authority," 6 pages, International Patent Appl. No. PCT/US2006/016538, European Patent Office (Feb. 27, 2007).
van Kamp et al., "Improvement by super disintegrants of the properties of tablets containing lactose, prepared by wet granulation," Pharmaceutisch Weekblad Scientific Edition; 1983, vol. 5, pp. 165-171.
Villa, "International Search Report," 4 pages, from International Appl. No. PCT/US2005/038328, European Patent Office, Rijswijk, The Netherlands (mailed Sep. 15, 2006).
Villa, "Written Opinion of the International Search Authority," 5 pages, from International Appl. No. PCT/US2005/038328, European Patent Office, Munich, Germany (mailed Sep. 15, 2006).
Vromans et al., "Studies on tableting properties of lactose," Pharmaceutisch Weekblad Scientific Edition; 1985, vol. 7, pp. 186-193.
Yamahara et al., "Effect of release rate on bioavailability of control-release multiple unit dosage forms," Yakuzaigaku 55(2):99-107 (1995).
Yamamoto et al., "The Effects of Nizatidine on the Function of Esophageal Motility in Patients with Gastroesophageal Reflux Disease (GERD)," Jpn. Pharmacol. Ther. 28(5):419-424 (2000).

(56) References Cited

OTHER PUBLICATIONS

Young, "International Preliminary Examination Report" 6 pages, PCT International Application No. PCT/US02/39238, United States Patent and Trademark Office (Apr. 27, 2005).

Young, "Written Opinion," 5 pages, PCT International Application No. PCT/US02/39238, United States Patent and Trademark Office (Jan. 13, 2005).

Zheng et al., "Influence of Eudragit® NE 30 D Blended with Eudragit® L 30 D-55 on the Release of Phenylpropanolamine Hydrochloride from Coated Pellets," Drug Development and Industrial Pharmacy 29(3):357-366 (2003).

Zimmer, "European Search Report," 3 pages, European patent appl. No. 01103129.1, European Patent Office (Jun. 9, 2001).

Zimmer, "International Search Report," 4 pages, PCT International Application No. PCT/US01/04012, European Patent Office (Jun. 19, 2001).

"International Search Report," 4 pages, PCT International Application No. PCT/USIB2010/003196, European Patent Office (Nov. 17, 2011).

"Written Opinion of the International Searching Authority," 5 pages, PCT International Application No. PCT/USIB2010/003196, European Patent Office (Nov. 17, 2011).

21st Edition Remington, "The Science and Practice of Pharmacy", P. Berringer, et al., pp. 896-903.

* cited by examiner

Figure 1
2.5X
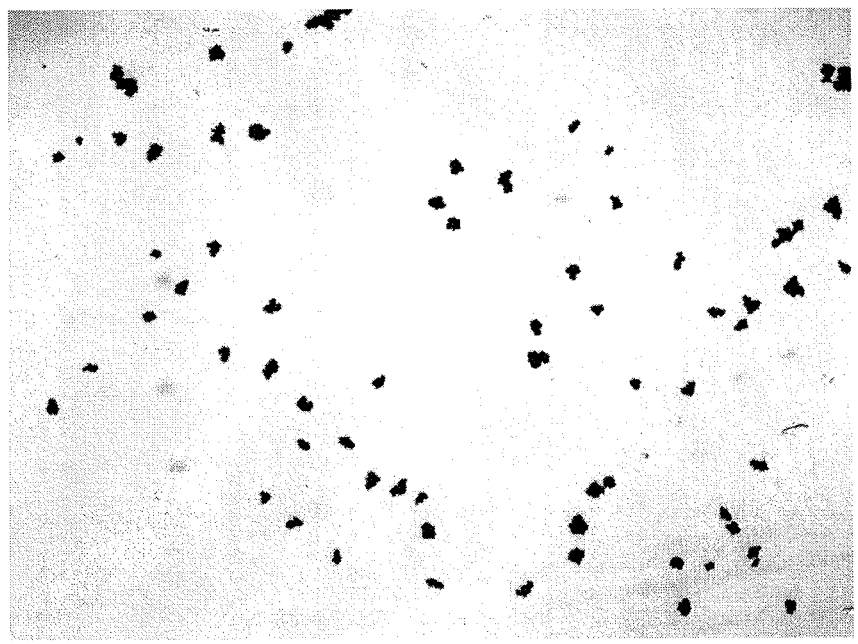
10X
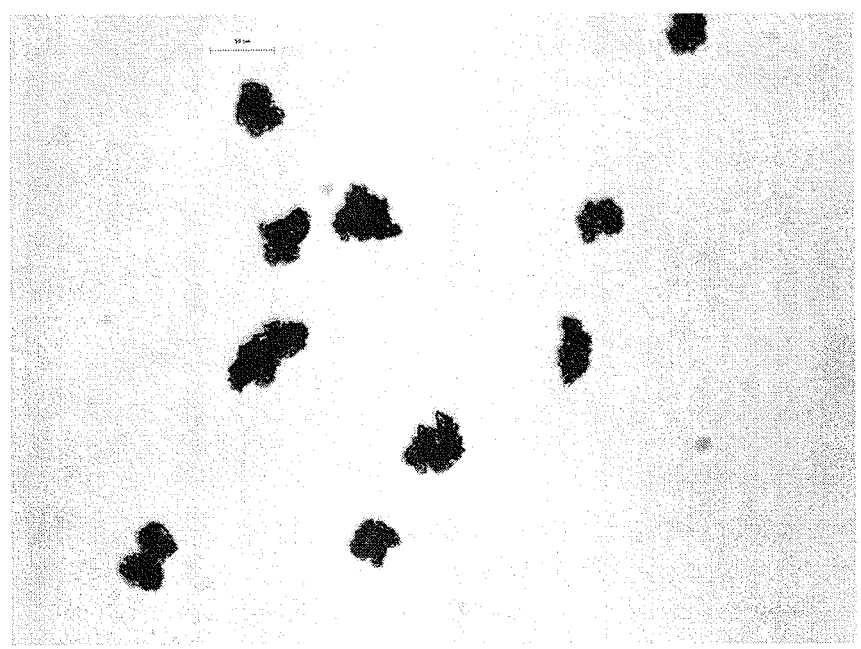

Figure 2
2.5x
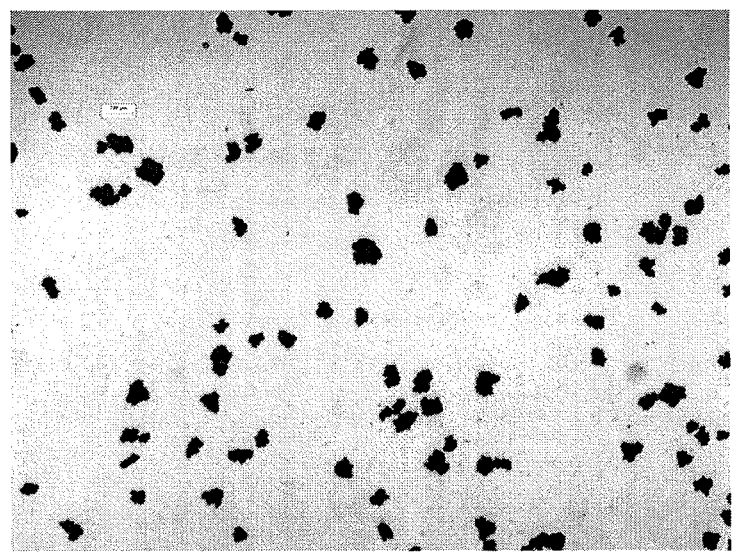
10x
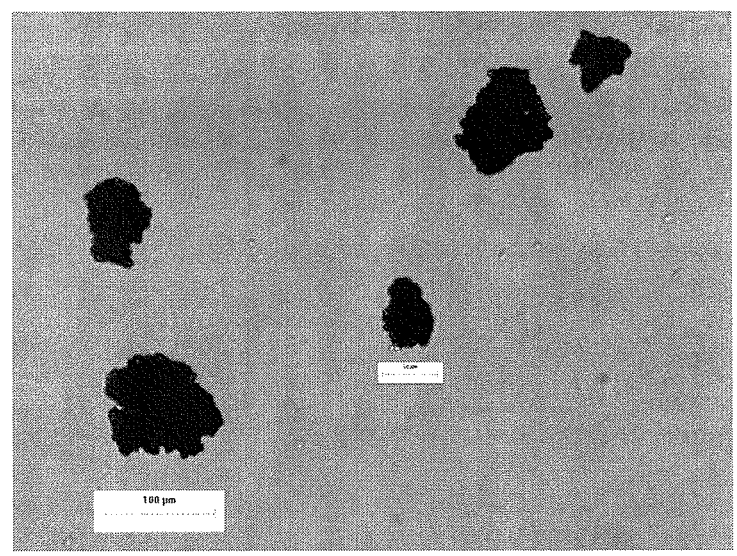

Figure 3
2.5x
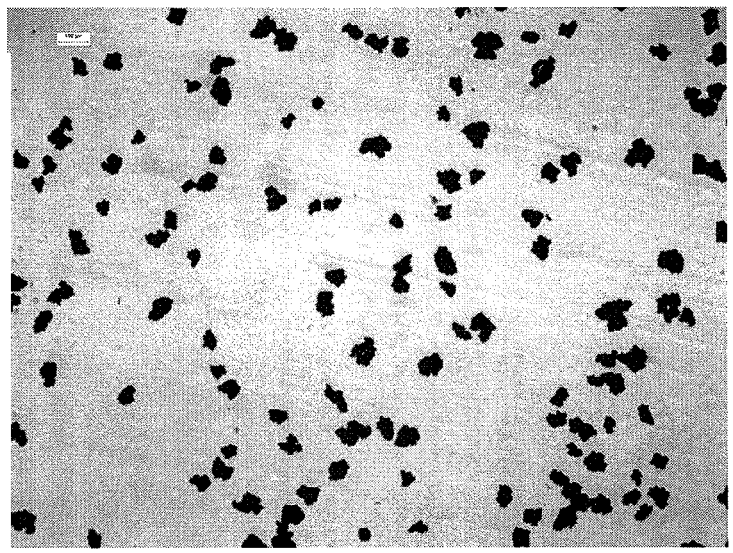
10x
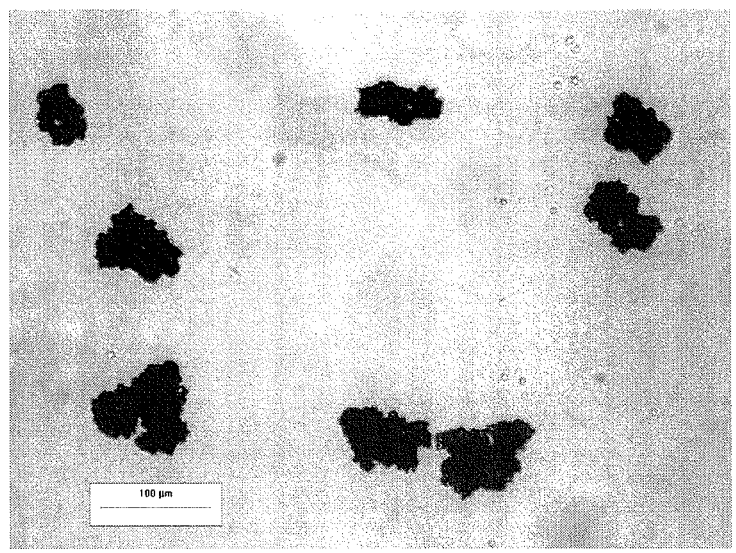

Figure 4
2.5x
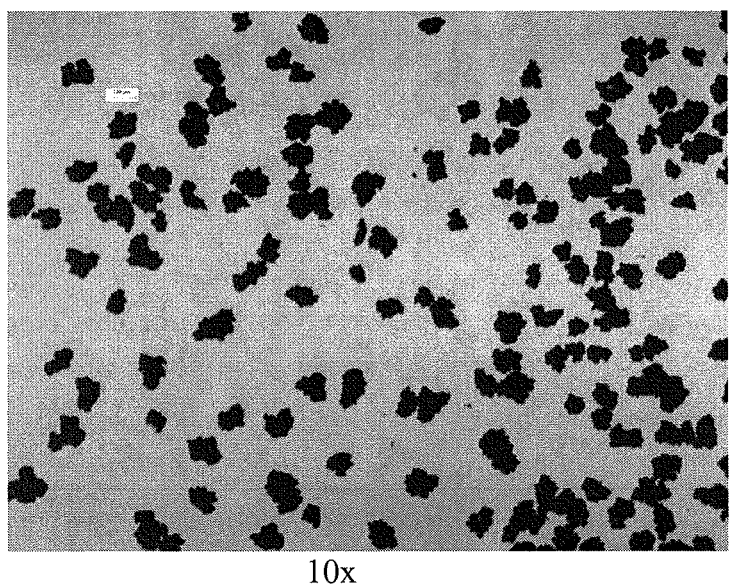
10x
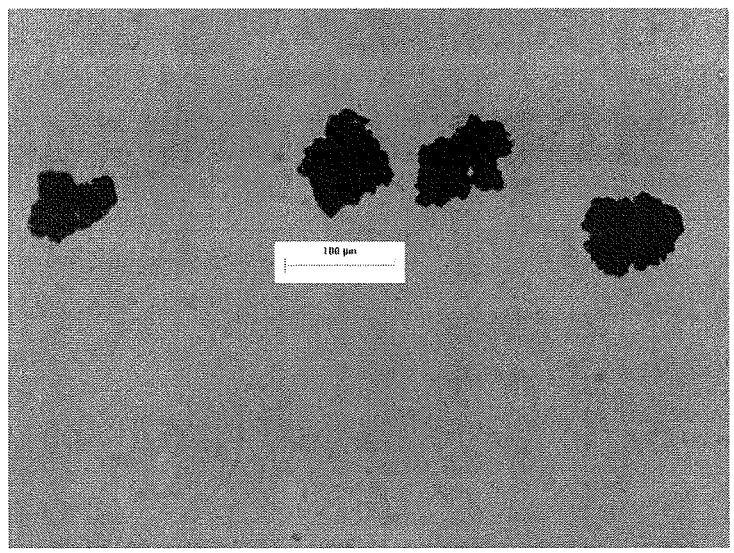

Figure 5
2.5x
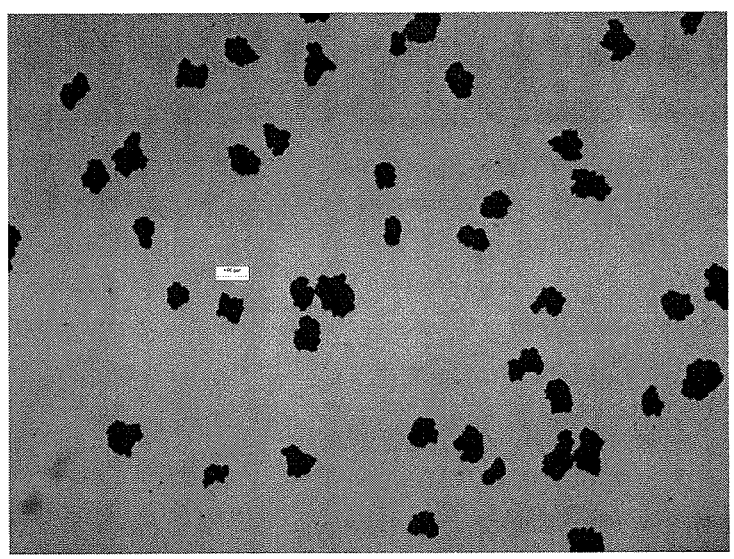
10x
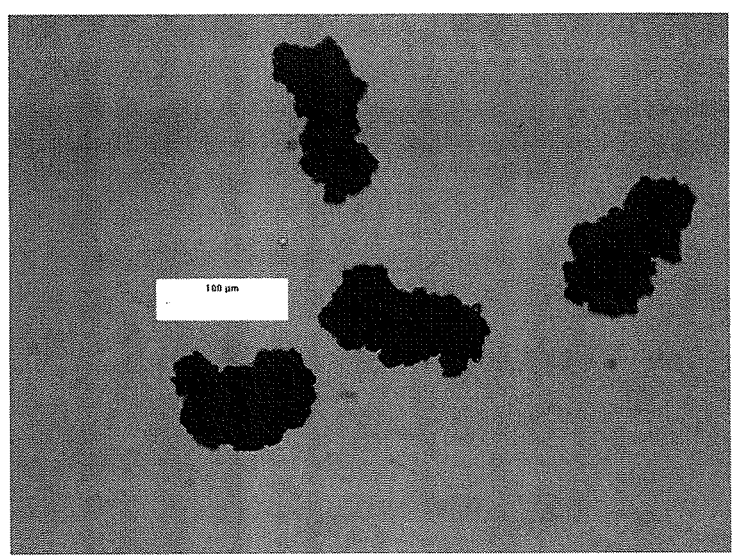

Figure 20

FEXOFENADINE MICROCAPSULES AND COMPOSITIONS CONTAINING THEM

CROSS-REFERENCE TO RELATED APPLICATIONS

The present application claims priority to U.S. Provisional Application No. 61/265,823 filed Dec. 2, 2009, U.S. Provisional Application No. 61/354,575 filed Jun. 14, 2010, each of which is herein incorporated by reference in its entirety for all purposes.

BACKGROUND

The most widely used dosage forms for oral administration include tablets and capsules. However, such dosage forms have several disadvantages. For example, it is estimated that 50% of the population have problems swallowing tablets (see Seager, 50 J. Pharmacol. and Pharm. 375-382 (1998)). In particular, it is difficult for some elderly persons to swallow tablets or capsules or to medicate children who are unable or unwilling to swallow tablets or capsules. This leads to poor or non-compliance with the treatment, and thus has a negative impact on the efficacy of the treatment.

The bitter taste of many actives also precludes medications from being easily sprinkled onto food, a commonly used method of administering medications to children. Bitter tasting drugs—incorporated into chewable tablets are typically thickly coated mostly with water-insoluble polymers, such as ethylcellulose, to taste mask the drugs through resisting fracturing of the coated drugs during tablet compression and/or during chewing and concomitant leakage of the bitter active. Consequently, substantially complete release of the drug from such chewable tablets in the gastrointestinal tract may take 2 hours or longer. More recently, orally disintegrating tablet (ODT) dosage forms have been introduced, which rapidly dissolve or disintegrate in the buccal cavity, and hence can be taken without water. Other convenient oral dosage forms include sachets and microparticle dispersions. Such medicines are convenient, particularly for the elderly and children.

Fexofenadine hydrochloride is a histamine H1 receptor antagonist, and is approved for the treatment of seasonal allergic rhinitis and chronic idiopathic urticaria. However, formulating fexofenadine is complicated by its low solubility at low pH (i.e., gastric) conditions. One typical way of addressing low solubility is to formulate the drug in ODT (orally disintegrating tablet) form. However, that approach is complicated by the bitter taste of fexofenadine hydrochloride.

U.S. Pat. No. 6,723,348 describes the preparation of an orodispersable tablet (ODT) containing fexofenadine in the form of fexofenadine granulated with additional excipients, then fluid bed coated with a polymer coating. However, the manufacturing process is relatively complex and requires multiple granulation, coating, and mixing steps.

It is an object of the present invention to provide microencapsulated fexofenadine, by a simple process, in a taste-masked immediate release form.

SUMMARY OF THE INVENTION

The present invention provides taste-masked immediate release microcapsules which comprise fexofenadine and a water-insoluble polymer coating and pharmaceutical composition comprising them. Co-granulated fexofenadine microcapsules are also disclosed in the present inventions. These microcapsules and the pharmaceutical compositions comprising them have suitable drug content and desirable pharmaceutical properties, including a quick dissolution rate of fexofenadine combined with a taste masking effect.

The present invention also provides a process for preparing the microcapsule and the co-granulated microcapsules and the pharmaceutical compositions comprising taste-masked immediate release microcapsules which comprise fexofenadine and a water-insoluble polymer coating. The process for microcapsules preparation includes the steps of: (a) dissolving a water-insoluble polymer in an organic solvent; (b) suspending fexofenadine in the organic solvent; (c) applying a coating of the water-insoluble polymer onto the fexofenadine by phase separation; and (d) separating the microcapsules from the organic solvent.

The pharmaceutical compositions of the present invention are useful for the treatment of inflammation-related conditions, such as seasonal allergic rhinitis and chronic idiopathic urticaria. Accordingly, the present invention also provides a method for treating an inflammation-related condition in an individual. The method comprises administering to an individual in need thereof a pharmaceutical composition comprising taste-masked immediate release microcapsules, wherein the microcapsules comprise fexofenadine and a water-insoluble polymer coating.

DETAILED DESCRIPTION OF THE INVENTION

All documents cited herein are incorporated by reference for all purposes.

As used herein, the term "coating weight" refers to the dry weight of the microcapsule coating divided by the weight of the entire microcapsule, multiplied by 100. For example, a coating weight of 20% means that for the given microcapsule, the coating constitutes 20% of the weight of the microcapsule.

As used herein, the term "average coating weight" refers to the mean value of the coating weight for a population of microcapsules. For example, if half of the microcapsules in a given population have a coating weight of 10% and the other half has a coating weight of 20%, the average coating weight for the given population of microcapsules is 15%.

As used herein, the term "microcapsules" refers to a drug (e.g., fexofenadine or a pharmaceutically salt, ester, and/or solvate thereof, or polymorph thereof) coated with a water-insoluble polymer coating.

As used herein, the term "microencapsulation" refers to a process of coating a drug with the water-insoluble polymer.

As used herein and unless otherwise specified, references to "fexofenadine" or a pharmaceutically acceptable salt, ester, and/or solvate thereof, or polymorph thereof.

As used herein, the term "API" means "active pharmaceutical ingredient", e.g., fexofenadine or a pharmaceutically salt, ester, and/or solvate thereof, or polymorphs thereof.

The present invention provides microcapsules of fexofenadine, a pharmaceutical composition comprising taste-masked immediate release microcapsules which comprise fexofenadine and a water-insoluble polymer coating. Microcapsules of fexofenadine may be in the form of co-granulated microcapsules and may comprise further inactive ingredients and excipients. In one embodiment of the present invention, the fexofenadine is fexofenadine hydrochloride.

The fexofenadine of the present invention may be crystalline or amorphous or combinations thereof. Any fexofenadine crystalline forms are included and can be used in the preparation of microcapsules, microcapsule granulate and co-granulated microcapsules of the present invention.

The water-insoluble polymer of the present invention may be any suitable, pharmaceutically acceptable water-insoluble polymer that forms a coating around the fexofenadine particles, and thereby yields fexofenadine microcapsules exhibiting taste-masked and immediate release properties. Examples of water-insoluble polymers which may be used in the present invention include ethylcellulose, polyvinyl acetate, cellulose acetate, cellulose acetate butyrate, polyvinyl acetate, ammonio-methacrylate copolymers and mixtures thereof. In one embodiment, the water-insoluble polymer of the invention is ethylcellulose.

The amount and type of polymer in the coating contributes toward regulating the release of the fexofenadine, making it possible to modulate the degree of taste masking and/or the fexofenadine release. In the present invention the coating polymer is insoluble in water. The average coating weight of the microcapsules of the present invention is from about 2% to about 40%, including about 5%, about 10%, about 13% about 15%, about 17%, about 18%, about 20%, about 25%, about 30%, about 35%, or about 40%. Typically, the average coating weight of the microcapsules of the present invention is from about 10% to about 20%. More typically, the average coating weight is from about 13% to about 18%. In one embodiment of the present invention, the microcapsules have an average coating weight of about 15%.

The wettability of the water insoluble coating of the microcapsules may be improved by treatment with surfactants. A surfactant layer may be applied to the microcapsules by suspending them in a solution containing the surfactant, or by fluid bed spraying process. The surfactant solution includes at least one surfactant and optionally other ingredients such as glidants or antisticking agents. The surfactant should be soluble in a solvent in which the coating polymer is practically insoluble under the relevant conditions, such as, for example, at room temperature. Suitable surfactants include sodium docusate (DOSS), sodium lauryl sulfate, sucrose fatty acid ester, Tween, Lutrol F68, sorbitan oleate, sorbitan laurate, etc. Other wetting agents may be chosen among: hydroxypropyl cellulose, polyethylene glycol 600, 1000, 3350, and 6000. In one embodiment, the surfactant is in one sense w/w % to about 10 w/w %. Typically, the concentration of surfactant in the solution is between about 0.25 w/w % and about 2 w/w %, or between about 0.5 w/w % and about 1.5 w/w % or between 0.45 and 0.75 w/w %. In one embodiment, the concentration of surfactant in the solution is about 0.45, in another about 0.6 w/w %, in another about 0.75%, in another about 1 w/w %, in still another about 1.5 w/w %. Methods for wetting are also described in U.S. Pat. No. 6,509,034. A particular antisticking agent is silicon dioxide.

If necessary, one or more further protective coating layers (e.g., Opadry Clear, etc.) may be applied onto the microcapsules of the invention.

A further embodiment of the present invention is a granulate of taste-masked fexofenadine microcapsules coated with a water-insoluble polymer.

In the present invention not less than 80% of the fexofenadine taste-masked immediate release microcapsules have a particle size distribution (PSD) below 500 microns; preferably not less than 80% of the microcapsules have a PSD below 355 microns; even preferably, not less than 80% of the microcapsules have a PSD below 250 microns. In a further embodiment not less than 80% of the microcapsules have particle size distribution below 200 microns. The taste masked immediate release microcapsules are also used for the preparation of the taste masked immediate release co-granulated microcapsules.

A further embodiment is a co-granulate of water insoluble coated microcapsules and at least one inactive ingredient. The co-granulates are obtained when the microcapsules are granulated with a portion of at least one inactive ingredient.

Inactive ingredients may be chosen for example from the group consisting of sugar alcohol and saccharides, such as sucrose, xanthan gum, beta-cyclodextrin, xylitol, sorbitol, mannitol, lactose, arabitol, isomalt, glycerol, alginate, microcrystalline cellulose, carboxymethylcellulose or a mixture thereof. Disintegrants in combination with sugar alcohols or saccharides may also be suitable inactive ingredients to be added to the fexofenadine microcapsules or co-granulates.

The microcapsule co-granulate disclosed herein is composed of microcapsules of fexofenadine having a water insoluble coating and at least one inactive ingredient. Particular embodiments of ratios of microcapsule: inactive ingredient(s) are between 1:3 and 1:10, between 1:5 and 1:8, and between 1:6 or 1:7.

The fexofenadine microcapsule co-granulate of the invention has a dissolution release comparable to that of the wetted microcapsules. In one embodiment the particle size of the co-granulate is preferably below 600 μm with a low amount of granules under 125 μm. The reduced amount of fine fraction is relevant as this fraction is almost totally composed of un-granulated microcapsules and the presence of high levels of this fraction could be correlated to a low homogeneity of the co-granulate.

In one embodiment the co-granulate has the following characteristics: ratio 1:7; homogeneity variation <5.0%; fine fraction below 125 μm <5.0%; fraction over 600 μm <10.0%; process yield about 97.0%. Another particular embodiment of the invention is where those co-granulates having the following characteristics: ratio 1:7; homogeneity variation <5.0%; fine fraction below 125 μm <5.0%; fraction over 600 μm <5.0%; process yield about 97.0%.

A further embodiment of the present invention is a blend of fexofenadine microcapsule co-granulate and at least an inactive ingredient granulate. The inactive ingredient granulate comprises one or more inactive ingredients, and may be chosen for example from the group consisting of sugar alcohol and saccharide, such as sucrose, xanthan gum, beta-cyclodextrin, xylitol, sorbitol, mannitol, lactose, arabitol, isomalt, glycerol, alginate, microcrystalline cellulose, carboxymethylcellulose or a mixture thereof. Disintegrants in combination with sugar alcohols or saccharides may also be suitable inactive ingredients to be added to the co-granulates. Preferably the blend (also called bulk mix) has the microcapsule co-granulate and the granulated inactive ingredient(s) in 1:1 ratio. The preferred co-granulate comprises fexofenadine microcapsule, sucrose and xanthan gum, and the granulated inactive ingredient comprises sucrose.

A further embodiment of the present invention is a pharmaceutical composition comprising the fexofenadine taste-masked microcapsules coated with a water insoluble polymer. Said composition comprises fexofenadine microcapsules and further at least one inactive ingredient that may be granulated or ungranulated and/or at least one excipient.

In one embodiment of the invention the pharmaceutical composition of the invention comprises fexofenadine microcapsule co-granulate blended with at least one inactive ingredient that may be granulated or ungranulated. A particular embodiment of the invention is where the pharmaceutical composition has co-granulates of microcapsules and at least one granulated inactive ingredient in 1:1 ratio.

The pharmaceutical compositions of the present invention provide immediate release of the active ingredient, for example, fexofenadine hydrochloride. In one embodiment, the compositions of the present invention release at least about 60% of the fexofenadine hydrochloride within 15 minutes in pH 6.8 JP 2° nd fluid (Japanese Pharmacopeia). In another embodiment, the compositions of the present invention release at least about 65% of the fexofenadine hydrochloride within 15 minutes in pH 6.8 JP 2° nd fluid. In still another embodiment, the compositions of the present invention release at least about 70% of the fexofenadine hydrochloride within 15 minutes in pH 6.8 JP 2° nd fluid. In yet another embodiment, the compositions of the present invention release at least about 75% of the fexofenadine hydrochloride within 15 minutes in pH 6.8 JP 2° nd fluid. In yet another embodiment, the compositions of the present invention release at least about 80% of the fexofenadine hydrochloride within 15 minutes in pH 6.8 JP 2° nd fluid. In yet another embodiment, the compositions of the present invention release at least about 85% of the fexofenadine hydrochloride within 15 minutes in pH 6.8 JP 2° nd fluid. In still embodiment, the compositions of the present invention release at least about 90% of the fexofenadine hydrochloride within 15 minutes in pH 6.8 JP 2° nd fluid. In another embodiment, the compositions of the present invention release at least about 95% of the fexofenadine hydrochloride within 15 minutes in pH 6.8 JP 2° nd fluid.

In another embodiment, the compositions described above may be combined with at least one additional pharmaceutical excipient. Excipients for use in the compositions or dosage forms of the present invention include fillers, diluents, glidants, disintegrants, binders, lubricants etc. Other pharmaceutically acceptable excipients include acidifying agents, alkalizing agents, preservatives, antioxidants, buffering agents, chelating agents, coloring agents, complexing agents, emulsifying and/or solubilizing agents, flavors and perfumes, humectants, sweetening agents, wetting agents etc.

Examples of suitable fillers, diluents and/or binders include, but are not limited to, lactose (e.g., spray-dried lactose, α-lactose, β-lactose, Tabletose®, various grades of Pharmatose®, Microtose® or Fast-Floc®), microcrystalline cellulose (e.g. Avicel PH101, Avicel PH102, Ceolus KG-802, Ceolus KG-1000, Prosolv SMCC 50 or SMCC90, various grades of Elcema®, Vivacel®, Ming Tai® or Solka-Floc®), hydroxypropylcellulose, L-hydroxypropylcellulose (low substituted), hydroxypropyl methylcellulose (HPMC) (e.g. Methocel E, F and K, Metolose SH of Shin-Etsu, Ltd, such as, e.g., the 4,000 cps grades of Methocel E and Metolose 60 SH, the 4,000 cps grades of Methocel F and Metolose 65 SH, the 4,000, 15,000 and 100,000 cps grades of Methocel K; and the 4,000, 15,000, 39,000 and 100,000 grades of Metolose 90 SH), methylcellulose polymers (such as, e.g., Methocel A, Methocel A4C, Methocel A15C, Methocel A4M), hydroxyethylcellulose, sodium carboxymethylcellulose, carboxymethylhydroxyethylcellulose and other cellulose derivatives, sucrose, xanthan gum, cyclodextrin (e.g., beta-cyclodextrin), agarose, sorbitol, mannitol, dextrins, maltodextrins, starches or modified starches (including potato starch, maize starch and rice starch), calcium phosphate (e.g., basic calcium phosphate, calcium hydrogen phosphate, dicalcium phosphate hydrate), calcium sulfate, calcium carbonate, sodium alginate, collagen etc. or combinations thereof.

Specific examples of diluents include, e.g., calcium carbonate, dibasic calcium phosphate, tribasic calcium phosphate, calcium sulfate, microcrystalline cellulose, powdered cellulose, dextrans, dextrin, dextrose, fructose, kaolin, lactose, mannitol, sorbitol, starch, pregelatinized starch, sucrose, xanthan gum, beta-cyclodextrin, etc. and combinations thereof.

Specific examples of glidants and lubricants include, e.g., silicon dioxide, stearic acid, magnesium stearate, calcium stearate or other metallic stearates, talc, waxes and glycerides, light mineral oil, PEG, glyceryl behenate, colloidal silica, hydrogenated vegetable oils, corn starch, sodium stearyl fumarate, polyethylene glycols, alkyl sulfates, sodium benzoate, sodium acetate etc.

Other excipients include, e.g., flavoring agents, coloring agents, taste-masking agents, pH-adjusting agents, buffering agents, preservatives, stabilizing agents, anti-oxidants, wetting agents, humidity-adjusting agents, surface-active agents, suspending agents, absorption enhancing agents, agents for modified release etc.

Non-limiting examples of flavoring agents include, e.g., cherry, orange, banana, strawberry or other acceptable fruit flavors, or mixtures of cherry, orange, and other acceptable fruit flavors, at up to, for instance, about 3% based on the tablet weight. In addition, the compositions of the present invention is can also include one or more sweeteners such as aspartame, sucralose, or other pharmaceutically acceptable sweeteners, or mixtures of such sweeteners, at up to about 2% by weight, based on the tablet weight. Furthermore, the compositions of the present invention can include one or more FD&C colorants at up to, for instance, 0.5% by weight, based on the tablet weight.

Antioxidants include, e.g., ascorbic acid, ascorbyl palmitate, butylated hydroxyanisole, butylated hydroxytoluene, hypophosphorous acid, monothioglycerol, potassium metabisulfite, propyl gallate, sodium formaldehyde sulfoxylate, sodium metabisulfite, sodium thiosulfate, sulfur dioxide, tocopherol, tocopherol acetate, tocopherol hemisuccinate, TPGS or other tocopherol derivatives, etc.

The fexofenadine microcapsules or the co-granulated microcapsules of the invention may be formulated into a variety of final dosage forms including tablets (e.g., orally disintegrating chewable, dispersible, fast dissolving, effervescent), hard gelatin capsules and sprinkle, suspensions, sachets for permanent or extemporaneous suspensions, and sachets for direct administration in the mouth.

The microcapsules or the co-granulated microcapsules of the invention or mixture thereof may also be formulated into a dry syrup in presence of suitable inactive ingredients and possible further excipients. A dry syrup formulation is a fast dissolving powder that is formulated for ease of swallowing. It may be administered directly in powder form, or first hydrated with a liquid, for example with 3-5 mL of water in a tablespoon or 15-50 mL of water in a glass. Methods of carrying out dry syrup formulations are described in U.S. Publication No. 2008/0064713, herein incorporated by reference for all purposes.

The preferred dry syrup consists of fexofenadine taste masked microcapsule co-granulate in 1:1 ratio to the granulated inactive ingredients; the co-granulate has the following characteristics: microcapsules are in ratio 1:7 to the inactive ingredient; the co-granulates contains sucrose and xanthan gum, the granulated inactive ingredient comprises sucrose. The fexofenadine dry syrup according to the present invention has physico-chemical properties such as particle size, dissolution rate the taste masking that are very little affected by the filling step. This dry syrup has high homogeneity. In one embodiment of the invention the co-granulate has homogeneity variation <5.0%; fine fraction below 125 μm <5.0%; fraction over 600 μm <5.0%; process yield about 97.0%;

The dry syrup is filled into sachet or stick-pack. A sachet is chosen according to the ability to properly dose the product, to the minimum filling weight achievable, to the impact of the mechanical stress on the granulate; to the use of different packaging configuration For flat sachet and the different filling weights any known packaging may be used. Particular filling weights are 300 and 600 mg, they are herein applied in the preparation of very low dosage strengths of the medicament (15 and 30 mg). The final packaging may have different configurations, such as stick pack or flat pack; one example of packaging may consist in five boxes in line linked together with a PE film.

The fexofenadine taste-masked microcapsules of the present invention may be prepared by coacervation, which is an effective technology for producing taste-masked microcapsules. The coacervation process involves salting out macromolecules into liquid-like colloidal droplets rather than solid or gel aggregates. Coacervation may be carried out as described in U.S. Pat. Nos. 5,252,337, 5,639,475, 6,139,865 and 6,495,160, the entire contents of which are expressly incorporated by reference herein for all purposes.

The microcapsules of the present invention may be prepared by providing a homogeneous solution of a water-insoluble polymer in a suitable solvent in which the active ingredient and, optionally, coating additives are dispersed in suspension. Phase separation may then be employed to cause insolubilization of the water-insoluble polymer, which gels (coacervates) around the active ingredient particles to form the microcapsules. Phase separation may be performed, for example, through variation in temperature or in pH or by adding to the organic solvent a phase-separation inducing agent (i.e., a phase inducer agent) that cause insolubilization of the water-insoluble polymer. Finally, the microcapsules obtained are subjected to hardening, if required, and recovered.

More specifically, the process for preparing taste-masked immediate release particles according to the present invention includes the following steps: (a) dissolving a water-insoluble polymer in an organic solvent; (b) suspending fexofenadine in the organic solvent; (c) applying a coating of the water-insoluble polymer onto the fexofenadine by phase separation; and (d) separating the microcapsules from said organic solvent, for example by filtering, centrifuging; and (e) removing residual organic solvent by drying the microcapsules.

As discussed above, the phase separation step may be carried out by variation in temperature or in pH, or by adding to the organic solvent a phase inducer agent that cause insolubilization of the water-insoluble polymer. In one embodiment, the phase separation step is performed by adding to the organic solvent a phase inducer agent. Suitable phase inducer agents which may be used in the present invention include polyethylene, polyisobutylene, butyl rubber, polybutadiene, isoprene methacrylic polymers, organosilicon polymers such as polydimethyl siloxane, paraffin, etc. In one embodiment, the phase inducer agent is polyethylene.

The organic solvent may be a single organic solvent or it may include a mixture of organic solvents. In accordance with the coacervation process, the organic solvent is chosen so as to dissolve the coating polymer, but not the active ingredient. Suitable organic solvents include cyclohexane or other hydrocarbon solvents. In one embodiment, the organic solvent is cyclohexane.

Non-limiting examples of suitable water-insoluble polymers include ethylcellulose, cellulose acetate, cellulose acetate butyrate, polyvinyl acetate, neutral methacrylic acid-methylmethacrylate copolymers, and mixtures thereof. In one embodiment of the process for preparing taste-masked immediate release particles according to the present invention, the water-insoluble polymer is ethylcellulose, the phase inducer agent is polyethylene, the solvent is cyclohexane and the fexofenadine is fexofenadine hydrochloride.

The taste masked fexofenadine microcapsules co-granulates are prepared by co-granulating the microcapsules (prepared as described above) with an inactive ingredient (eg sugar alcohol and/or saccharide) in form of fine powder in a fluid bed by spraying a binder solution. The process comprises the following steps: 1) microencapsulating of fexofenadine; 2) optional wetting of the microcapsules; 3) adding wetted or unwetted fexofenadine microcapsules to inactive ingredient(s); 4) spraying of the binding solution; 5) drying of the granules; and 6) sieving of the granules.

Granulation may be carried out in a conventional granulator according to conventional techniques. The binder solution is composed of one or more inactive ingredients, preferably is composed of two inactive ingredients; this is particularly suitable to obtain an efficient granulation of the microcapsule with the sucrose. The binder solution is preferably composed of sucrose and xanthan gum. Other inactive ingredients may be chosen from the group consisting of sugars, sugars alcohols, saccharides, sugar/sugar alcohol in combination with disintegrants.

The following parameters are kept under control during this process: the amount of binder solution; the ratio between wet microcapsules and the inactive ingredient(s); the spray rate of the binding solution; the atomization pressure; the air flow. The drying of the granules is performed under the same controlled conditions of inlet air temperature, inlet air flow, etc. The granules are sieved trough a stainless steel net of 840 µm.

The co-granulate is then blended with the inactive ingredient(s) granulate. The final blend comprises the above co-granulate and the inactive ingredient(s) granulate. In a particular embodiment this pharmaceutical composition has the co-granulate and the granulated inactive ingredient(s) in a 1:1 ratio.

Particular inactive ingredient(s) granulate is composed of sucrose. The granulate is obtained by a process comprising the following steps: 1) adding the inactive ingredient(s); 2) spraying of the binding solution; 3) drying of the granules; and 4) sieving and calibrating. During this process the following experimental conditions are controlled: the amount of powder granulated; the spray rate of the solution; the atomization pressure; and the humidity of the in-let air. The air flow is kept constant. All the drying steps are performed in the same conditions (inlet air temperature, inlet air flow, etc.). The granules are sieved trough a stainless steel net of 600 µm or 840 µm. The granules bigger than 840 µm are forced trough a 600 µm screen granulator.

The mixing of the co-granulate, the inactive ingredient(s) granules, together with further ingredients (such as flavour, glidants) is performed under controlled rotation speed for suitable mixing time.

The process of preparation of fexofenadine dry syrup comprises the following different steps: 1) microencapsulating fexofenadine 2) optional wetting of microcapsules; 3) co-granulating of wetted or unwetted microcapsules with at least one inactive ingredient (such as sucrose); 4) separately granulating of inactive ingredient(s) (such as sucrose); 5) mixing of co-granulate of fexofenadine obtained in step 3) together with the granulated inactive ingredient(s) (such as sucrose) obtained in step 4) and with optional further ingredients (such as flavors and silicon dioxide); and 6) filling of fexofenadine dry syrup bulk mixture of step 5) in sachets.

The present invention further provides a method for treating an inflammation-related condition in an individual. The method comprises administering to an individual in need thereof a pharmaceutical composition comprising taste-masked immediate release microcapsules, wherein the microcapsules comprise fexofenadine and a water-insoluble polymer coating. Inflammation-related conditions which may be treated according to the present invention include seasonal allergic rhinitis and chronic idiopathic urticaria.

The dose of fexofenadine hydrochloride to be administered to an individual may vary depending on the age of the individual being treated as well as the indication. Common doses of fexofenadine hydrochloride are 15 mg twice daily, 30 mg twice daily, 60 mg twice daily and 180 mg once daily. Consequently, final dosage forms prepared with the compositions of the present invention may include, for example, 15 mg of fexofenadine hydrochloride, 30 mg of fexofenadine hydrochloride, 60 mg of fexofenadine hydrochloride or 180 mg of fexofenadine hydrochloride.

The following examples are provided for purposes of illustration, and should in no way be construed to limit the present invention.

BRIEF DESCRIPTION OF THE FIGURES

FIG. 1: Photomicrographs of fexofenadine microcapsules in cyclohexane Sample 1 (average Ethylcellulose weight 10%).

FIG. 2: Photomicrographs of fexofenadine microcapsules in cyclohexane Sample 2 (average Ethylcellulose weight 13%).

FIG. 3: Photomicrographs of fexofenadine microcapsules in cyclohexane Sample 3 (average Ethylcellulose weight 15%).

FIG. 4: Photomicrographs of fexofenadine microcapsules in cyclohexane Sample 5 (average Ethylcellulose weight 17%).

FIG. 5: Photomicrographs of fexofenadine microcapsules in cyclohexane Sample 6 (average Ethylcellulose weight 20%).

EXPERIMENTAL PART

1. Fexofenadine Microcapsules
1.1 Methods and Equipment for Fexofenadine Microcapsules Preparation Cyclohexane is poured into the microencapsulation reactor. Then, under continuous stirring, fexofenadine HCl, ethylcellulose (EC) and polyethylene are added. The mixture is heated and then cooled down. Microcapsules are recovered, and then washed (one or more times), filtered, and dried over night (about 16 h) in a fume hood or in a hood at 40° C. The powder is sieved through a 300 μm opening sieve.

TABLE 1

The Process Flow Sheet

| COMPONENT | STEP | EQUIPMENT |
|---|---|---|
| Fexofenadine, Ethylcellulose, Epolene[1], Cyclohexane[2] | COACERVATING with PHASE SEPARATION | Reactor Temperature emo controlling system Stirrer, |
|  | WASHING | Filtering system |
|  | FILTERING | Filtering system |
|  | DRYING | Hood, Oven |
|  | SIEVING | Sieve |

[1]removed during washing step
[2]removed during drying step

Several batches of microcapsules are prepared; the amount of the ethylcellulose coating (% w/w, calculated as microcapsule weight gain) in the final microcapsules is summarized in Table 2.

TABLE 2

Average Coating Weight of Microcapsules

| Lot | Coating Weight (%) |
|---|---|
| SAMPLE 1 | 10 |
| SAMPLE 2 | 13 |

TABLE 2-continued

Average Coating Weight of Microcapsules

| Lot | Coating Weight (%) |
|---|---|
| SAMPLE 3 | 15 |
| SAMPLE 4 | 15 |
| SAMPLE 5 | 17 |
| SAMPLE 6 | 20 |
| SAMPLE 7 | 20 |

The microcapsules are characterized by appearance, particle size distribution, residual solvent content and dissolution rate. Microscopic evaluation at the end of the microencapsulation process of the five batches shows appropriate polymer coating deposition around the fexofenadine particles consistent with the amount of the polymer that is used to prepare the different batches (see FIGS. 1-5).

Figure 6:
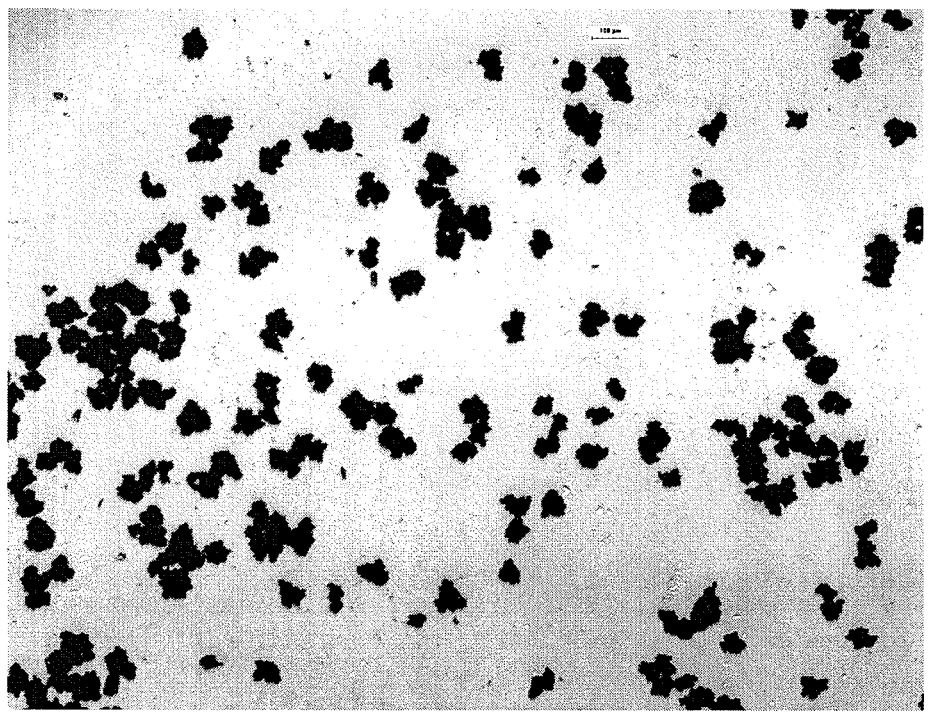
FIG. 6: Photomicrograph of microcapsule Sample 4—15% Ethylcellulose (magnification 2.5×).
Figure 7:
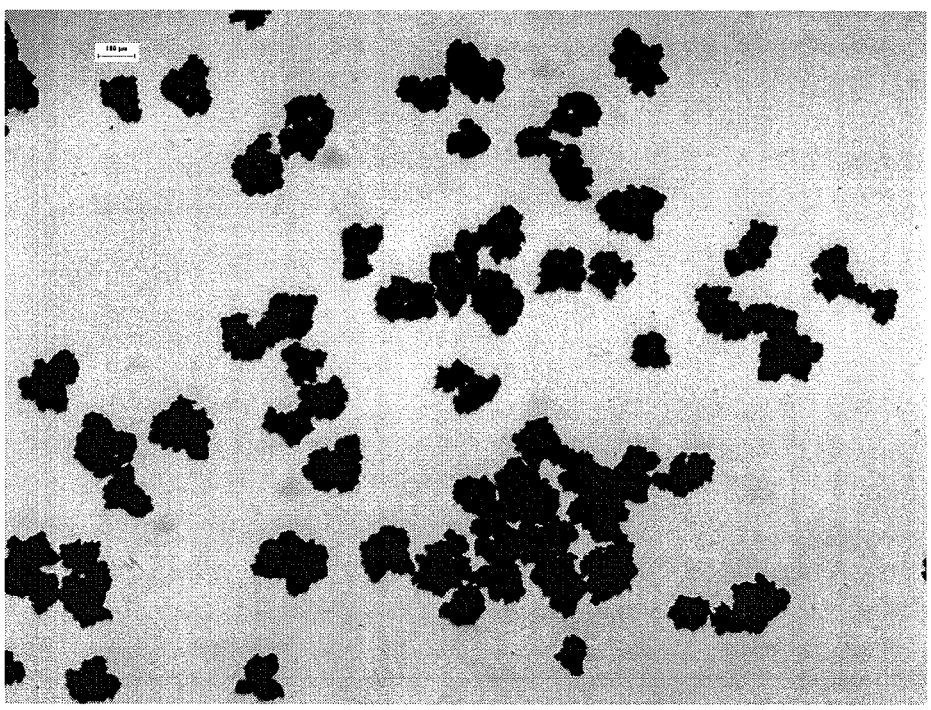
FIG. 7: Photomicrograph of microcapsule Sample 7—20% Ethylcellulose (magnification 2.5×).

As shown in FIGS. 6 and 7, an increase in particle size and level of agglomeration of the microcapsules is found to be proportional to the amount of polymeric coating that is applied. The very small particles of fexofenadine undergo a process akin to granulation, and form discrete particulate clusters in the 50 to 200 micron size range; cluster size is seen to increase with polymer level.

Figure 8:
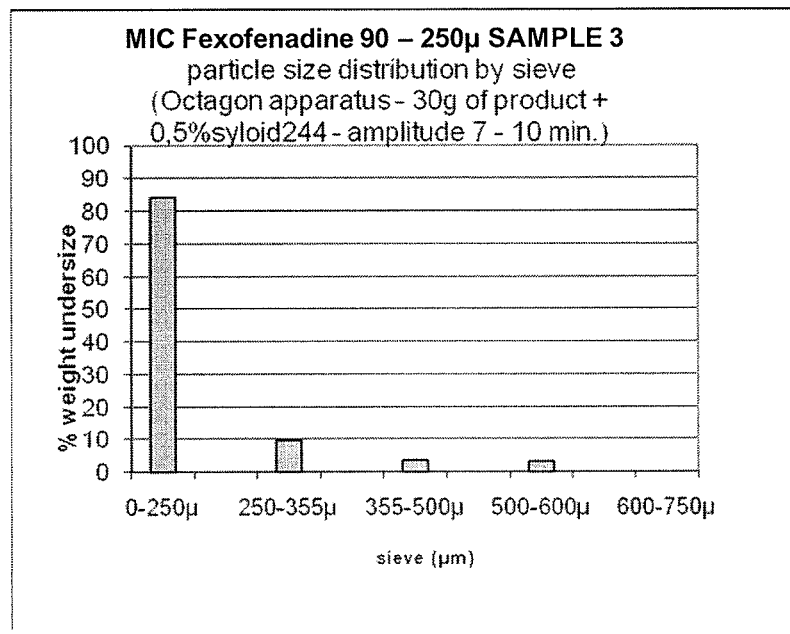
FIG. 8: The particle size distribution (PSD) of microcapsules with a 15% Ethylcellulose.

The particle size distribution (PSD) of microcapsules with a 15% coating is measured (generated from SAMPLE 3). An amount of microcapsules in the range of 25 g-50 g is poured into a 100 mL HDPE bottle, 0.2% (w/w) of Syloid 244 (colloidal silicon dioxide, WR Grace, Columbia, Md.) is sieved through 150 µm screens, added to the microcapsules and manually blended for 2 minutes. The mixture of microcapsules and Syloid 244 is sieved with a digital Octagon apparatus for 10 minutes at amplitude 7. The results are reported in FIG. 8. The fine fraction of the microcapsules above 250 micron is not less than 80%.

TABLE 3

Assay Values for Fexofenadine in Microcapsule Batches with Varied Coating Levels

| | Assay (mg/g) | |
|---|---|---|
| Sample | Found | Theoretical |
| SAMPLE 8 (13% average coating weight) | 832.7 | 852.9 |
| SAMPLE 9-D (17% average coating weight) | 802.1 | 813.7 |
| SAMPLE 6-D2 (20% average coating weight) | 767.3 | 784.3 |

As shown in Table 3 the assay values of the microcapsules are close to the theoretical values (98-99%).

The amount of residual solvent (cyclohexane) is always below 100 ppm for all microcapsules that are prepared in laboratory scale.

1.2 Industrial Scale Microencapsulation

Fexofenadine microcapsules at different levels of ethylcellulose (15, 18 and 20%) are prepared by the coacervation process in an 80 gallon stainless reactor, and using a fluid bed apparatus for the drying step. Fexofenadine HCl (code 1) and Fexofenadine HCl (code 2)) are used for the preparation of microcapsules. Microcapsules with a 15% ethylcellulose are prepared (Sample 71); the "in vitro" dissolution of SAMPLE 72 and SAMPLE 73 (both are prepared with a different starting fexofenadine (code 2). No significant differences are discerned between the microcapsules that are prepared with different API batches (Mann-Whitney non parametric statistical analysis, p=0.05).

Microcapsules with ethylcellulose levels of 15, 18, and 20% are produced. The microencapsulation trials are carried out by placing the API and the inactive ingredient(s) into the 80 gallon reactor, then adding fresh cyclohexane. The temperature parameters and stirring conditions of the cycle are set as previously described. At the end of the thermal cycle, the paddle rotation is stopped and the product is allowed to settle. The supernatant is removed using a vacuum pump, and fresh solvent is added. The mixture is stirred for short time. Subsequently, the microcapsules are allowed to precipitate again and part of the cyclohexane is removed for a second time. The microcapsules are then filtered in a fluid bed equipped with a 70 µm stainless steel sieve on the bottom under inert nitrogen atmosphere and under-vacuum. After the solvent removal, the microcapsule slurry is dried in the same fluid bed to a residual cyclohexane level below 3000 ppm. The product that is obtained is manually discharged from the fluid bed chamber and sieved through a 840 µm stainless steel sieve.

TABLE 4

Microcapsules batch compositions.

| Material (Kg) | SAMPLE 74 15% EC | SAMPLE 75 15% EC | SAMPLE 76 15% EC | SAMPLE 77 15% EC |
|---|---|---|---|---|
| Fexofenadine | 28.33 | 28.33 | 28.33 | 28.33 |
| Ethylcellulose | 5.00 | 5.00 | 5.00 | 5.00 |
| Wash | No | No | Yes | Yes |
| Assay-experimental (mg/g) | 836.7 | 825.9 | 832.3 | 850.7 |

Figure 9:
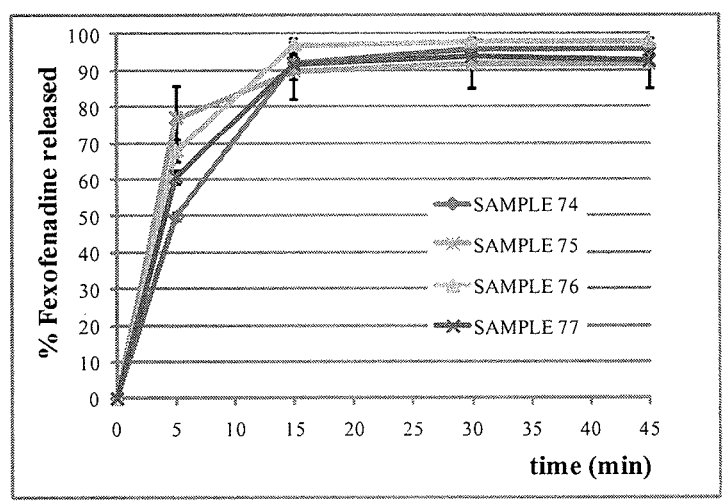
FIG. 9: The dissolution profiles of fexofenadine microcapsules, Ethylcellulose 15%, in buffer pH 6.8 $2^{nd}$ fluid JP (n=6)

The dissolution profiles of fexofenadine microcapsules in buffer pH 6.8 2nd fluid JP (ethylcellulose level 15%) are displayed in FIG. 9.

1.3 Dissolution Test of Microcapsules

The microcapsule prototypes have improved wettability when a small amount of a surfactant such as DOSS is added to the dissolution media.

Dissolution tests on microcapsules are performed by adding a small amount of surfactants to the dissolution media.

Figure 10:
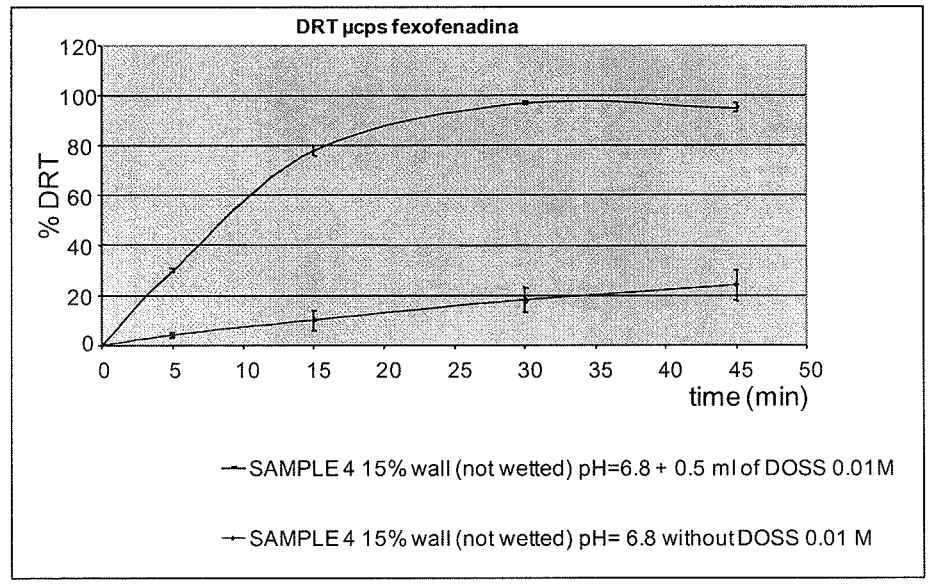
FIG. 10: Dissolution profiles of fexofenadine microcapsules, with or without 0.5 mL of DOSS 0.01M in the dissolution media.

FIG. 10 shows the dissolution profile of microcapsules having a 15% EC (SAMPLE 4) with or without 0.5 mL of DOSS 0.01M in the dissolution media.

Comparison with dissolution rates of commercial Allegra® tablet formulations is carried out using a USP paddle is reported in Table 5.

TABLE 5

Dissolution of Fexofenadine Microcapsule and Allegra® Tablets

| | | % drug released (SD) | | | |
|---|---|---|---|---|---|
| Sample | EC | 5 min. | 15 min. | 30 min. | 45 min. |
| SAMPLE 7 | 20% | 17 (1) | 46 (4) | 77 (6) | 88 (2) |
| SAMPLE 4 | 15% | 30 (1) | 78 (2) | 97 (1) | 95 (2) |
| SAMPLE 1 | 10% | 92 (1) | 97 (1) | 96 (1) | 96 (1) |
| *Allegra® tablets | | 79 (3) | 96 (3) | 98 (3) | 98 (3) |

*Without addition of 0.5 mL of 0.01M DOSS solution.

This comparison indicates that at 15% and 10% ethylcellulose levels, the dissolution of microencapsulated fexofenadine is similar to that of the tablet formulations. Taste evaluation indicates that a 15% coating provides acceptable taste characteristics.

Dissolution values using an official analytical dissolution method using a pH 6.8 buffer (2° nd Fluid for dissolution test, JP15) and assays of the different batches of microcapsules are summarized in tables 6-8.

TABLE 6

Microcapsules with 15% EC Assay and Dissolution Rate

| | Assay (mg/g) | | buffer pH 6.8 JP 2° fluid + 0.5 mL DOSS 0.01M % drug released (SD) | | | |
|---|---|---|---|---|---|---|
| Sample | Theoretical value | Analytical value | 5 min | 15 min | 30 min | 45 min |
| SAMPLE 4 | 850 | 848.0 | 30 (1) | 78 (2) | 97 (1) | 95 (2) |
| SAMPLE 10 | 850 | 840.6 | 31 (2) | 74 (6) | 94 (2) | 96 (1) |
| SAMPLE 11 | 850 | 843.7 | 38 (2) | 85 (9) | 98 (2) | 98 (2) |

Microcapsules with a 15% ethylcellulose are prepared (SAMPLE 71) and wetted (by the in-situ process at lab scale, SAMPLE 71/A) and dissolution compared in Table

TABLE 7

Microcapsules with 17% EC Assay and Dissolution Rate

| | Assay (mg/g) | | buffer pH 6.8 JP 2° fluid + 0.5 mL DOSS 0.01M % drug released (SD) | | | |
|---|---|---|---|---|---|---|
| Batch | Theoretical value | Analytical value | 5 min | 15 min | 30 min | 45 min |
| SAMPLE 12 | 830 | 824.7 | 22 (2) | 56 (3) | 83 (2) | 92 (1) |
| SAMPLE 13 | 830 | 826.7 | 23 (2) | 58 (7) | 82 (3) | 91 (1) |
| SAMPLE 9 | 830 | 815.3 | 23 (1) | 55 (1) | 85 (4) | 93 (1) |

1.4 Wetted Microcapsules Preparation

The hydrophobic nature of ethylcellulose gives rise to some drawbacks when the microcapsules are used in aqueous environment. When the finished dosage form containing such microcapsules is placed into a glass of water, the hydrophobic microcapsules tend to float and form aggregates (e.g. clumps or cluster) and some tend to attach to the glass wall.

The improved wettability of the microcapsules is achieved by treating the microcapsules with a minimal amount of a surfactant (Wetting Treatment). Several different wetting ingredients are investigated (e.g., sodium lauryl sulfate; sodium docusate; sucrose fatty acid ester; hydroxypropylcellulose and polyethylene glycol 600, 1000, 3350 and 6000, Lutrol F68; etc.).

Wetted treatment of the microcapsules that is performed with surfactants is carried out either by suspending the microcapsules in a surfactant solution, or by spraying the microcapsules with a surfactant solution using for example a fluid bed coating as described below or other suitable equipment.

Wetting process by suspension. The process is carried out by suspending the microcapsules (e.g., SAMPLE 3, 15% average coating weight) in docusate sodium (DOSS) diluted solutions in cyclohexane. The suspension is mixed for about 15 min at 200 rpm, and Syloid 244 is then added to the mixture with stirring. The microcapsules are recovered by filtration using standard equipment. The microcapsules are then dried at room temperature for about 16 hours and sieved using a 300 micron sieve. The DOSS solution that is added to the microcapsules preferably contains more than 0.25% of DOSS. The following lots are prepared: SAMPLE 8 (13% average coating weight), SAMPLE 19-D (15% average coating weight) SAMPLE 9-D (17% average coating weight) and SAMPLE 6-D (20% average coating weight).

Wetting process by fluid bed. The process is performed using a fluid bed coater that is equipped with a Wurster Insert, and coating microcapsules with a surfactant solution according to standard spraying procedures. The treated microcapsules are then sieved through a 300 micron sieve. SAMPLE 20-D, having 15% average EC weight, is prepared. Wetted microcapsules that are obtained are readily suspendable in aqueous environment without giving rise to significant aggregation and water repellence. Reproducibility of the wetting treatment is checked by dissolution testing. "in vitro" dissolution values, assay and impurity of the batches of microcapsules are checked as is reported in the following part.

Laboratory-Scaled Wetting Treatment The wetting process is carried out in a top-spray fluid bed apparatus by applying an aqueous solution of sodium docusate and dispersed silicon dioxide. Three different levels of surfactants: 0.45, 0.60 and 0.75%, are applied onto 400 g of microcapsules SAMPLE 78 (15% EC). The results that are obtained are listed in Table 8.

TABLE 8

"In vitro" dissolution values and drug assay for different batches.

| Batch | Na Docusate (%) | Silicon Dioxide (%) | Fexofenadine (mg/g) | DRT buffer pH 6.8 2nd fluid JP | | | | |
|---|---|---|---|---|---|---|---|---|
| | | | | 5 min | 10 min | 15 min | 30 min | 45 min |
| SAMPLE 14 | 0.75% | 2.25% | 824.5 | 82 ± 2 | 95 ± 2 | 94 ± 1 | 95 ± 1 | 94 ± 1 |
| SAMPLE 15 | 0.60% | 2.27% | 825.7 | 84 ± 1 | 94 ± 2 | 94 ± 1 | 94 ± 1 | 93 ± 1 |
| SAMPLE 16 | 0.45% | 2.27% | 826.8 | 76 ± 2 | 91 ± 1 | 93 ± 1 | 93 ± 1 | 93 ± 1 |

Figure 11:
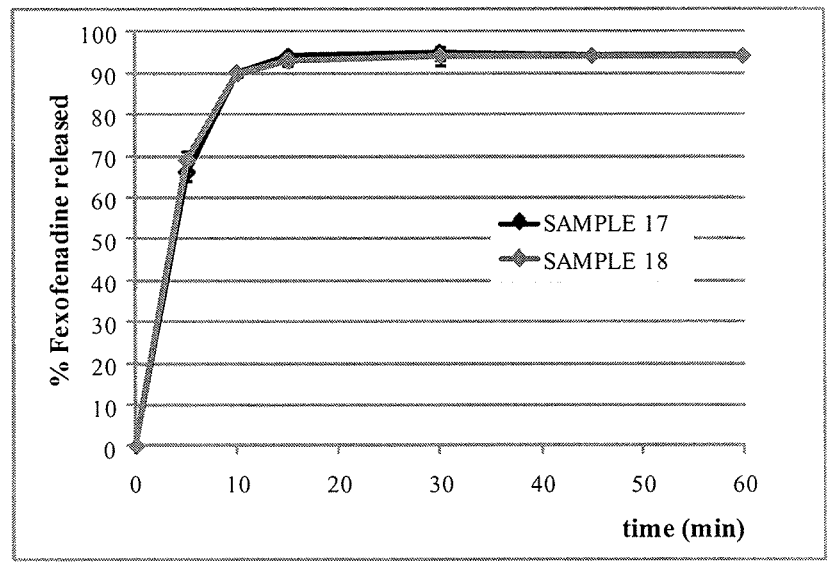
FIG. 11: Dissolution profiles of fexofenadine from industrial wetted microcapsules buffer pH 6.8 $2^{nd}$ fluid JP (n=6).

Industrial-Scaled Wetting Treatment. The wetting treatment is carried out at an industrial scale directly onto an 18 inch fluid bed apparatus, and a series of wetted microcapsules batches SAMPLE 17 and SAMPLE 18 are produced. The wetting dispersion is loaded into the fluid bed using a Watson-Marlow pump equipped with a Marprene© tube. The theoretical composition is reported in Table 9 and the dissolution profiles are showed in Table 10 and FIG. 11 respectively. Additionally, the water content (Karl Fisher analysis) of SAMPLE 18 is measured (0.38%).

TABLE 9

Theoretical composition of industrial wetted microcapsules.

| batch | Fexofenadine mic (%) | Docusate (%) | Silicon Dioxide (%) | Drug Assay (mg/g) | DOSS Assay (mg/g) |
|---|---|---|---|---|---|
| SAMPLE 17 | SAMPLE 78 (coating 15%) 97.13 | 0.60 | 2.27 | 805.2 ± 3.3 | 5.9 ± 0.1 |
| SAMPLE 18 | SAMPLE 78 (coating 15%) 97.13 | 0.60 | 2.27 | 819.7 ± 1.8 | 5.7 ± 0.2 |

TABLE 10

"In vitro" dissolution values of industrial wetted microcapsules.

Values in buffer pH 6.8 $2^{nd}$ fluid JP

| batch | 5 min | 10 min | 15 min | 30 min | 45 min | 60 min |
|---|---|---|---|---|---|---|
| SAMPLE 17 | 66 ± 3 | 90 ± 2 | 94 ± 1 | 95 ± 1 | 94 ± 1 | 94 ± 1 |
| SAMPLE 18 | 69 ± 1 | 90 ± 2 | 93 ± 1 | 94 ± 0 | 94 ± 0 | 94 ± 1 |

1.5 Analysis and Dissolution Test of Wetted Microcapsules
Assay and impurities are analyzed for different samples

TABLE 11

Total Impurities of Wetted Microcapsules Prepared with Different Amounts of EC

| | Impurity (%) | | |
|---|---|---|---|
| Sample | MDL 102,038 | Unknown. | Total |
| SAMPLE 8 (13% coat) | 0.03 | 0.05 | 0.08 |
| SAMPLE 9-D (17% coat) | 0.03 | 0.04 | 0.07 |
| SAMPLE 6-D2 (20% coat) | 0.04 | 0.05 | 0.09 |

As shown in Table 11 the assay values of the wetted microcapsules are close to the theoretical values (98-99%) and the total level of impurities is lower than 0.1% for all samples tested.

Figure 12:
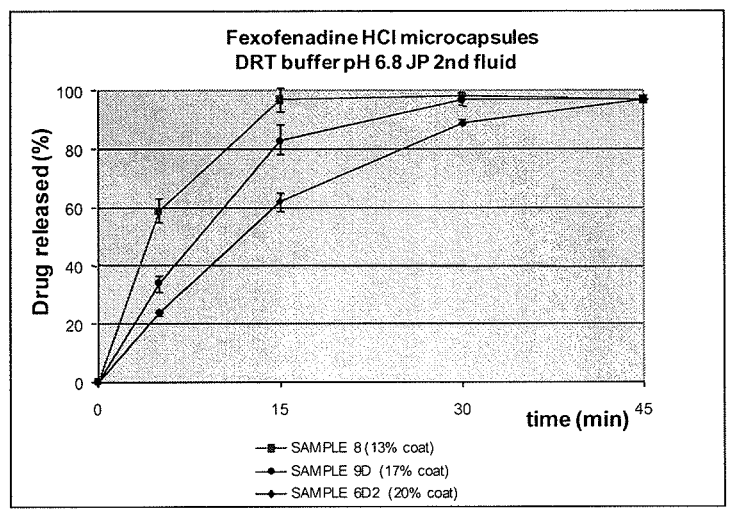
FIG. 12: Dissolution rate of fexofenadine from microcapsules with three different average Ethylcellulose weight levels.

The dissolution of wetted microcapsules is carried out using pH 6.8 JP 2° nd fluid. These results are summarized in Table 12 below and some of them are also presented as a graph in FIG. 12.

TABLE 12

Percent Fexofenadine Release from wetted Microcapsules at Various Time Points for Four Different Ethylcellulose Levels

| | Drug release % (SD) n = 3 | | | | |
|---|---|---|---|---|---|
| Sample | 0 min | 5 min | 15 min | 30 min | 45 min |
| SAMPLE 8 (13% coat) | 0 | 59 (4) | 97 (4) | 98 (1) | 97 (1) |
| SAMPLE 19-D (15% coat) | 0 | 44 (2) | 90 (3) | 97 (1) | 96 (1) |
| SAMPLE 9-D (17% coat) | 0 | 34 (3) | 83 (5) | 97 (2) | 97 (1) |
| SAMPLE 6-D2 (20% coat) | 0 | 24 (1) | 62 (3) | 89 (1) | 97 (1) |
| -SAMPLE 20-D (15% coat) | 0 | 81 (4) | 95 (2) | 95 (2) | 95 (2) |

Figure 13:
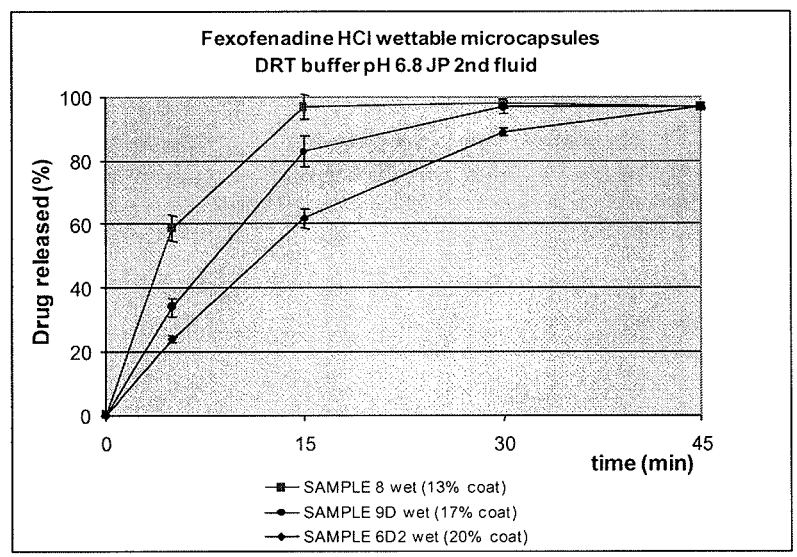
FIG. 13: Dissolution profiles at pH 6.8 2° nd fluid JP of wettable microcapsules at different Ethylcellulose levels.

Samples with average coating weight levels of 13%, 15% and 17% release 80% of the fexofenadine within 15 minutes. The dissolution rate is consistent with the EC level; that is, samples with higher coating levels exhibit a slower dissolution rate, while samples with lower coating levels exhibit a more rapid rate of release. Notably, the batch is treated with a surfactant applied with fluid bed (SAMPLE 20-D) has a faster release rate (80% release within 5 minutes) (see also FIG. 13)

Assay of the batches of wetted microcapsules and their "in vitro" dissolution values are summarized in Tables 13-20.

TABLE 13

Assay of Microcapsules with 13% EC with Wetting Treatment

| | Assay (mg/g) | |
|---|---|---|
| Sample | Theoretical value | Analytical value |
| SAMPLE 21-D | 852.9 | 826.2 |
| SAMPLE 22--D | 852.9 | 826.0 |
| SAMPLE 23-D | 852.9 | 832.7 |

TABLE 14

Assay of Microcapsules with 15% EC with Wetting Treatment

| | Assay (mg/g) | |
|---|---|---|
| Sample | Theoretical value | Analytical value |
| SAMPLE 24--D | 833.3 | N.A. |
| SAMPLE 11-D | 833.3 | 828.9 |
| SAMPLE 25--D1 | 833.3 | N.A: |
| SAMPLE 26-D1 | 833.3 | N.A. |

TABLE 15

Assay of Microcapsules with 17% EC with Wetting Treatment

| | Assay (mg/g) | |
|---|---|---|
| Sample | Theoretical value | Analytical value |
| SAMPLE 12D | 813.7 | 799.6 |
| SAMPLE 13-D | 813.7 | 805.1 |
| SAMPLE 9-D | 813.7 | 802.1 |

TABLE 16

Assay of Microcapsules with 20% EC with Wetting Treatment

| | Assay (mg/g) | |
|---|---|---|
| Sample | Theoretical value | Analytical value |
| SAMPLE 6-D2 | 784.3 | 767.3 |
| SAMPLE 27-D | 784.3 | N.A. |

TABLE 17

"In vitro" dissolution values of Microcapsules with 13% EC with Wetting Treatment

| | buffer pH 6.8 JP 2° fluid. No surfactant added drug released (SD) n = 3 | | | |
|---|---|---|---|---|
| Sample | 5 min | 15 min | 30 min | 45 min |
| SAMPLE 21-D | 60 (3) | 95 (1) | 96 (2) | 95 (1) |
| SAMPLE 22D | 55 (5) | 95 (1) | 96 (1) | 96 (1) |

TABLE 18

"In vitro" dissolution values of Microcapsules with 15% EC with Wetting Treatment

| | buffer pH 6.8 JP 2° fluid. No surfactant added drug released (SD) n = 3 | | | |
|---|---|---|---|---|
| Sample | 5 min | 15 min | 30 min | 45 min |
| SAMPLE 24--D | 52 (1) | 95 (1) | 98 (1) | 98 (1) |
| SAMPLE 11-D | 47 (2) | 93 (3) | 97 (1) | 97 (1) |
| SAMPLE 25--D1 | 51 (4) | 92 (2) | 96 (1) | 95 (1) |
| SAMPLE 26--D1 | 44 (2) | 90 (3) | 97 (1) | 96 (1) |

TABLE 19

"In vitro" dissolution values of Microcapsules with 17% EC with Wetting Treatment

| | buffer pH 6.8 JP 2° fluid. No surfactant added drug released (SD) n = 3 | | | |
|---|---|---|---|---|
| Sample | 5 min | 15 min | 30 min | 45 min |
| SAMPLE 12-D | 30 (2) | 77 (7) | 98 (2) | 99 (1) |
| SAMPLE 13--D | 33 (2) | 82 (3) | 99 (2) | 99 (1) |

TABLE 20

"In vitro" dissolution values of Microcapsules with 20% EC with Wetting Treatment

| | buffer pH 6.8 JP 2° fluid. No surfactant added drug released (SD) n = 3 | | | |
|---|---|---|---|---|
| Sample | 5 min | 15 min | 30 min | 45 min |
| SAMPLE 27-D | 20 (1) | 56 (2) | 85 (1) | 96 (1) |

"In vitro" dissolution values are in agreement with amount of ethylcellulose that is applied. Batch to batch variability, among the samples with the same coating level, is significantly reduced due to the improved wettability and dispersion capability of the microcapsules. By comparing dissolution profile of these wetted microcapsules with the corresponding unwetted microcapsules it is shown that these wetted microcapsules in surfactant-free medium exhibit a higher dissolution profile (Tables 21-24).

TABLE 21

"In vitro" dissolution values of Microcapsules with 13% Ethylcellulose with or without Wetting Treatment

| Sample | Mic Wetted | 0.5 ml DOSS 0.01M Added | buffer pH 6.8 JP 2° fluid % drug released (SD) | | | |
|---|---|---|---|---|---|---|
| | | | 5 min | 15 min | 30 min | 45 min |
| SAMPLE 21 | no | Yes | 50 (1) | 94 (2) | 97 (1) | 96 (1) |
| SAMPLE 21-D | yes | No | 60 (3) | 95 (1) | 96 (2) | 95 (1) |

TABLE 22

"In vitro" dissolution values of Microcapsules with 15% Ethylcellulose with or without Wetting Treatment

| Sample | Mic Wetted | 0.5 ml DOSS 0.01M Added | buffer pH 6.8 JP 2° fluid % drug released (SD) | | | |
|---|---|---|---|---|---|---|
| | | | 5 min | 15 min | 30 min | 45 min |
| SAMPLE 11 | no | Yes | 38 (2) | 85 (9) | 98 (2) | 98 (2) |
| SAMPLE 28-D | yes | No | 47 (2) | 93 (3) | 97 (1) | 97 (1) |

TABLE 23

"In vitro" dissolution values of Microcapsules with 17% Ethylcellulose with or without Wetting Treatment

| Sample | Mic Wetted | 0.5 ml DOSS 0.01M Added | buffer pH 6.8 JP 2° fluid % drug released (SD) | | | |
|---|---|---|---|---|---|---|
| | | | 5 min | 15 min | 30 min | 45 min |
| SAMPLE 12 | No | Yes | 22 (2) | 56 (3) | 83 (2) | 92 (1) |
| SAMPLE 12-D | Yes | No | 30 (2) | 77 (7) | 98 (2) | 99 (1) |

TABLE 24

"In vitro" dissolution values of Microcapsules with 20% Ethylcellulose with or without Wetting Treatment

| Sample | Mic Wetted | 0.5 ml DOSS 0.01M Added | buffer pH 6.8 JP 2° fluid % drug released (SD) | | | |
|---|---|---|---|---|---|---|
| | | | 5 min | 15 min | 30 min | 45 min |
| SAMPLE 27 | No | Yes | 15 (1) | 39 (3) | 63 (4) | 83 (6) |
| SAMPLE 27-D | Yes | No | 20 (1) | 56 (2) | 85 (1) | 96 (1) |

Figure 14:
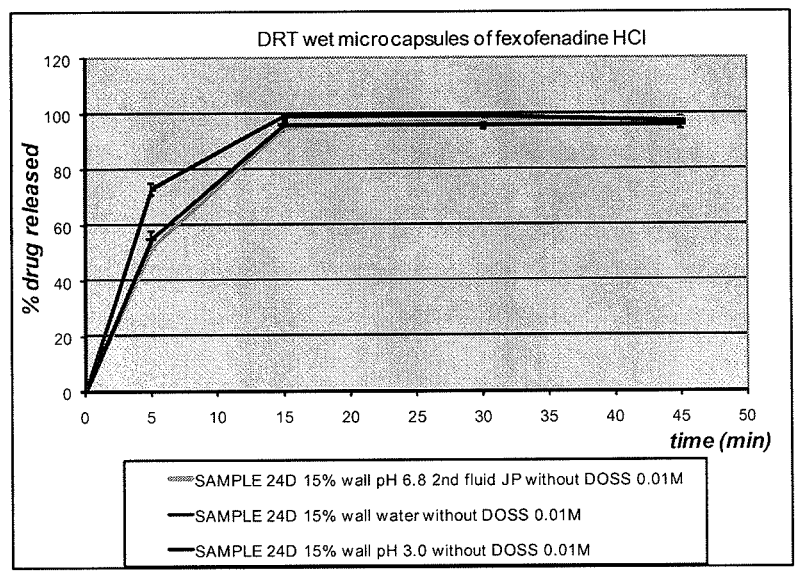
FIG. 14: Dissolution profiles of fexofenadine microcapsules in different dissolution media.

Wetted microcapsules demonstrate acceptable wettability and dispersibility in all media that are tested, without the need of adding surfactant to the dissolution media buffer. FIG. 14 compares the dissolution profiles of microcapsules of fexofenadine in different media with and without wetting treatment.

From the above data it can be evinced that: small taste masked microcapsules (about 200 μm) are easily dispersible in water; moreover, a suitable release profile is achieved.

1.6 Residual Solvent Microcapsules Batch Analysis

The residual cyclohexane on wetted and unwetted microcapsules that are prepared with different coating levels is measured at less than 100 ppm, based on the weight of the microcapsules. Data are summarized in Table 25:

TABLE 25

Residual Solvent of Wetted and Unwetted Microcapsules Prepared with Different Amounts of Ethylcellulose

| Sample | Ethylcellulose | Wetting treatment | Residual Cyclohexane |
|---|---|---|---|
| SAMPLE 12 | 17% | no | 21 ppm |
| SAMPLE 12--D | 17% | yes | 15 ppm |
| SAMPLE 11 | 15% | no | 26 ppm |
| SAMPLE 11-D | 15% | yes | 17 ppm |
| SAMPLE 6-D2 | 20% | yes | 13 ppm |
| SAMPLE 29 | 25% | no | 27 ppm |
| SAMPLE 29--D | 25% | Yes | 36 ppm |

From the above it is clear that residual cyclohexane is within ICH limits, as is reported in the Q3C(R3) guideline.

2. Preparation of Formulated Fexofenadine Microcapsules

Fexofenadine microcapsules are formulated with a series of external inactive ingredient(s) and/or excipient(s) to prepare and characterize prototype granulates that: 1) are compatible with the microcapsules; 2) further reduce the bitter taste of fexofenadine; 3) make the microcapsules easier to swallow; 4) make the microcapsules easier to disperse in water; and/or 5) obtain microcapsules which are easily dispersed and suspended in water.

2.1 Inactive Ingredient(s) Selection

The selection of the inactive ingredient(s) is made and binary blends of fexofenadine and the evaluated inactive ingredient(s) are prepared in various drug-to-inactive ingredient(s) ratios and stored at 50° C., wet and dry conditions in hermetically sealed glass vials. At fixed times the chemical stability of the blends is evaluated by HPLC test. Generally the results indicate that the API with the selected inactive ingredient(s) are reasonably stable under standard temperature and humidity conditions.

Different inactive ingredient(s) are also used to evaluate the ability of microcapsules to be dispersed/suspended (20 mL of distilled water, 36 mg of microcapsules), they are reported in Table 26):

TABLE 26

Visual Evaluation of Suspension/Dispersion of Fexofenadine Microcapsule Combined with Different Inactive ingredient(s)

| Inactive ingredient(s) | Suspension Quality |
|---|---|
| Sucrose | Good |
| Xylitol | Good |
| Sorbitol | Fair |
| Mannitol | Fair |
| Lactose Monohydrate | Good |
| MCC and sodium carboxymEthylcellulose (Ceolus ®RC-A591NF) | Fair |
| β-Cyclodextrin | Good |

Two formulation approaches are carried out: Direct blend of fexofenadine microcapsules with granulated product (excipients) and fluid bed granulation of fexofenadine with part of the sucrose to be further blended with additional granulated sucrose up to final dilution.

2.2 Granulates Preparation and Analysis

Three types of granulates are produced by top-spray fluid bed: 1) a sucrose granulate (SG); 2) a sucrose-xanthan gum granulate (SXG); and 3) a sucrose-β cyclodextrin granulate (SβCD). The fluid bed granulation technique is selected to produce soft granules with a uniform particle size and with the ability to dissolve rapidly in water.

Figure 15:
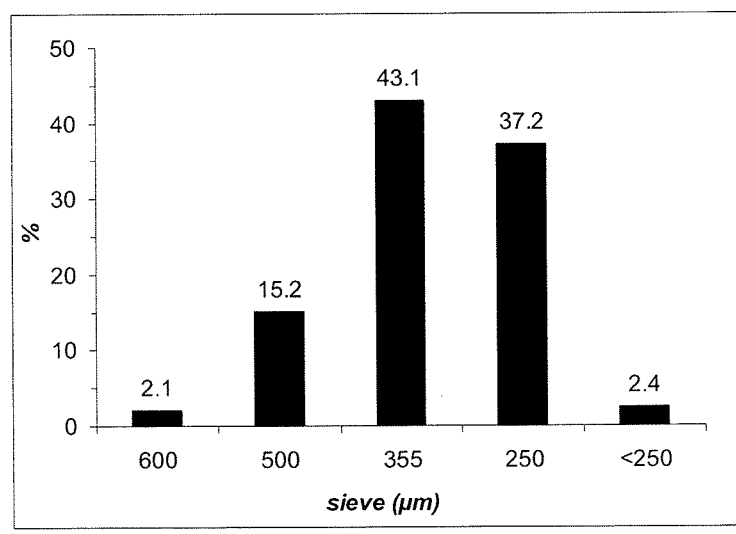
FIG. 15: Particle size analysis of SG granulate (SAMPLE 68), fraction selected 250-600 μm.

SG is obtained by granulating the sucrose with an aqueous solution of sucrose (5% w/w). The resulting product is dried and the granule fraction between 250-600 μm is selected. The particle size and bulk density (0.5 g/mL) of the resulting granules are characterized (FIG. 15).

Figure 16:
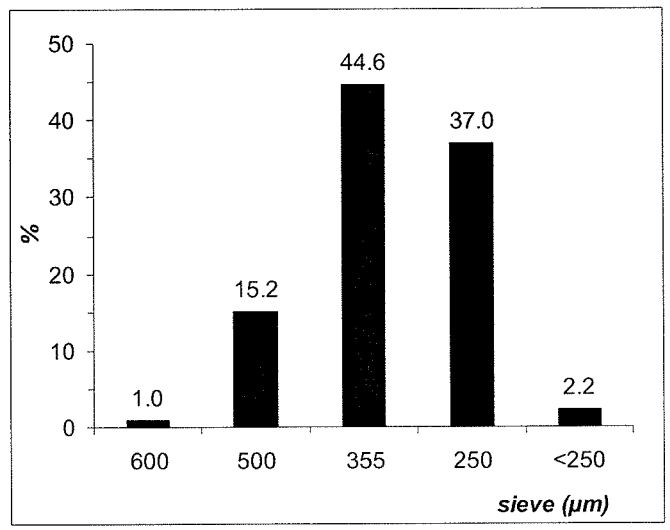
FIG. 16: Particle size analysis of SGX granulate (SAMPLE 69), fraction selected 250-600 μm.

SXG is prepared by granulating the sucrose first with an aqueous solution of sucrose (5% w/w) and then with aqueous-alcoholic suspension of xanthan gum. The resulting product is dried and the granule fraction between 250-600 μm is selected. the particle size, bulk density (0.5 g/mL) and residual ethanol content (<100 ppm) of the resulting granulate are characterized (FIG. 16)

Figure 17:
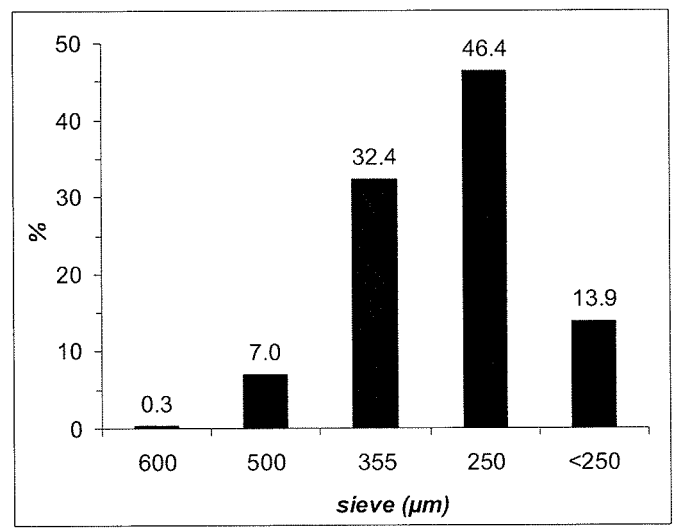
FIG. 17: Particle size analysis of SβCD granulate (SAMPLE 70), fraction selected 250-600 μm.

SβCD is produced by granulating a powder mixture of sucrose and β-cyclodextrin (2:1 w/w) with an aqueous solution of sucrose (5% w/w). The resulting product is dried and the granule fraction between 250-600 μm is selected. the particle size and bulk density (0.4 g/mL) of the resulting product are evaluated (FIG. 17).

The compositions of these three granulates are described in Table 27.

TABLE 27

Theoretical Composition of Granulates

| | SG | SGX | SβCD |
|---|---|---|---|
| Sucrose | 100.0% | 98.5% | 66.8% |
| Xanthan Gum | — | 1.5% | — |
| β cyclodextrin | — | — | 33.2% |

2.3 Preparation of Fexofenadine Microcapsule/Granulates Mixtures 2.3.1 First Set of Examples of Fexofenadine Microcapsule Blended with SGX, SG and SBCD Granulates)

The samples are prepared using fexofenadine HCl microcapsules at three different average EC weight levels (13%, 17% and 20%). All samples contain a co-granule of xanthan gum and sucrose (400 mg). In addition to these materials, each sample contains a quantity of sucrose granules (150 mg) either alone or in combination with an additional inactive ingredient(s), such as, for example, β-cyclodextrin (Beta CDX). The only exception to this is SAMPLE 39, which did not contain any additional sucrose granules.

Additional excipients are added in SAMPLE 30, SAMPLE 31, SAMPLE 32, SAMPLE 33 and SAMPLE 34. Flavorings are added to SAMPLE 30 and SAMPLE 31, while β-cyclodextrin (BCD) is added to SAMPLE 32, SAMPLE 33 and SAMPLE 34.

A placebo sample is also prepared (SAMPLE 35). It contains microencapsulated talc instead of fexofenadine HCl. Table 28, below, summarizes the qualitative and quantitative compositions of the batches.

TABLE 28

Composition of the Batches

| Sachet Prototype | Microcapsule Batch | EC % | Mg | Granules Sucrose + Xantham Gum (SGX) | Granules Sucrose (SG) | Granule Sucrose + BCD (SBCD) | Granule Sucrose + Yoghurt | Granules Sucrose + Strawberry | mg/sachet |
|---|---|---|---|---|---|---|---|---|---|
| SAMPLE 32 | SAMPLE 23--D | 13 | 36.0 | 400 | | 150 | | | 586.0 |
| SAMPLE 36 | SAMPLE 23--D | 13 | 36.0 | 400 | 150 | | | | 586.0 |
| SAMPLE 39 | SAMPLE 9--D | 17 | 37.4 | 400 | | | | | 437.4 |
| SAMPLE 33 | SAMPLE 9--D | 17 | 37.4 | 400 | | 150 | | | 587.4 |
| SAMPLE 37 | SAMPLE 9--D | 17 | 37.4 | 400 | 150 | | | | 587.4 |
| SAMPLE 35 | U9A032_E 36 | Placebo | 36.0 | 400 | 150 | | | | 586.0 |
| SAMPLE 34 | SAMPLE 23--D | 13 | 36.0 | 400 | | 150 | | | 586.0 |
| SAMPLE 38 | SAMPLE 6--D2 | 20 | 38.5 | 400 | 150 | | | | 588.5 |
| SAMPLE 30 | SAMPLE 6--D2 | 20 | 38.5 | 400 | | | | 150 | 588.5 |
| SAMPLE 31 | SAMPLE 6--D2 | 20 | 38.5 | 400 | | | 150 | | 588.5 |

Homogeneity of dispersion of the resulting granules are characterized before and after agitation/stirring in 20 mL of water.

Additionally, criteria such as sedimentation/settling/floating, re-suspension ability, residual after pouring, and dissolution at pH 6.8 JP, 1 mM HCl (pH 3.0) and distilled water of the fexofenadine microcapsule/granulate mixture are evaluated as well.

The wettability and dispersion test is performed in 50 mL glass beaker with 20 mL of de-mineralized water at room temperature (20-25° C.). Specifically, an amount of microcapsules corresponding to 30 mg of fexofenadine HCl and the selected inactive ingredient(s) is weighed and poured into the beaker. The mixture is gently stirred for 10 seconds and the tendency to form agglomerates, floating, settling, sinking is observed for 30 seconds. Finally, the suspension is stirred again for 2 seconds and poured out, and any residue in the beaker is evaluated. Finally the mouth feel and taste masking characteristics of the fexofenadine microcapsule/granulate mixture is evaluated by administering the powder into the mouth or on a tablespoon with few milliliters of water. The maximum amount of external inactive ingredient(s) and/or excipients that is added to these batches of fexofenadine microcapsules (≅36 mg) is 550 mg.

2.3.1.1 Dissolution of Fexofenadine Microcapsules/Granulates Mixtures

A series of tests are carried out using fexofenadine microcapsules coated with an amount of ethylcellulose ranging from 13% to 20%, and blended with the three different types of granules, as described above in Table 28. The wettability/dispersion trials show that the combination of granulates with the fexofenadine microcapsules did not have a negative impact on their wettability and dispersion in water. Furthermore, good dispersability is shown for the formulations using a limited amount of liquid (tablespoon).

SAMPLE 35 is a placebo prepared with microcapsules of talc instead of fexofenadine HCl. SAMPLE 34 has the same composition as SAMPLE 32, and is prepared to confirm the taste masking capability of the microcapsules with the lowest coating level. All the prototypes are prepared with granules of SXG. The SβCD granulate is used in some samples (SAMPLE 32, SAMPLE 33, SAMPLE 34) to evaluate the influence of this inactive ingredient(s) on the reduction of bitterness. SAMPLE 39 is prepared with a reduced level of inactive ingredient(s) to evaluate the effects of inactive ingredient(s) level on mouth feel. Flavored prototypes SAMPLE 30 and SAMPLE 31 are also evaluated. The dissolution profiles of the samples are reported in the following tables and Figures.

Taste masking tests indicated that all samples generate an immediate sweet sensation, followed by a slight bitterness (after 20-30 sec). However this bitter taste is not recognized as unpleasant.

Figure 18:
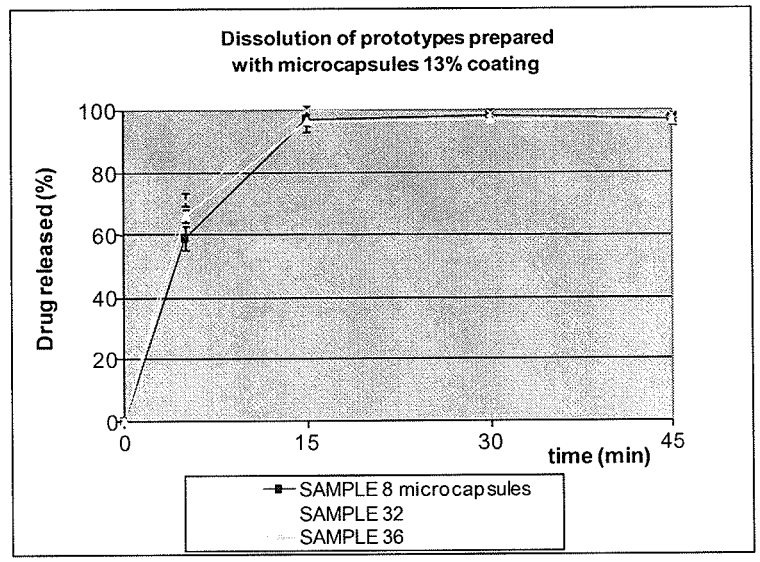
FIG. 18: Dissolution rate of fexofenadine from microcapsules with 13% average ethylcellulose weight.
Figure 19:
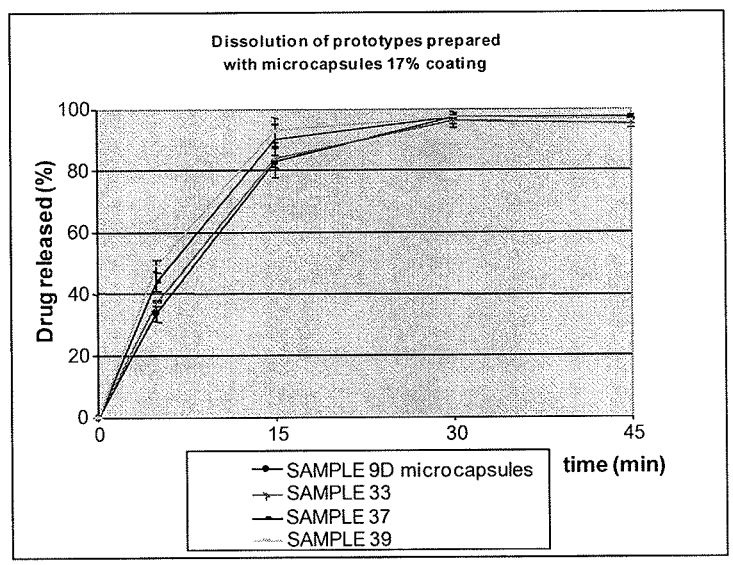
FIG. 19: Dissolution rate of fexofenadine from formulations containing microcapsules with 17% average ethylcellulose weight.

The results of the dissolution of fexofenadine microcapsules/granulates mixtures with a 13%, 17%, 20% of polymer is carried out using pH 6.8 JP 2° nd fluid are summarized in Table 29-31 and also presented as a graph in FIG. 18, 19, 20. These results are compared to those that are obtained with unformulated microcapsules.

TABLE 29

Percent Fexofenadine Release from Microcapsules and Two Fexofenadine microcapsules/granulates mixtures Using Microcapsules with an Average Ethylcellulose Weight of 13%

| | Drug release % (SD) n = 3 | | | | |
|---|---|---|---|---|---|
| Sample | 0 min | 5 min | 15 min | 30 min | 45 min |
| SAMPLE 8 (microcapsules) | 0 | 59 (4) | 97 (4) | 98 (1) | 97 (1) |
| SAMPLE 32 | 0 | 66 (2) | 96 (1) | 97 (1) | 96 (1) |
| SAMPLE 36 | 0 | 71 (2) | 100 (1) | 99 (1) | 98 (1) |

The dissolution characteristics of the products are similar to that of the microcapsules with a small increase in dissolution rate recorded overall.

TABLE 30

Percent Fexofenadine Release from Microcapsules and Two Fexofenadine microcapsules/granulates mixtures using Microcapsules with an Average EC Weight of 17%

| | Drug release % (SD) n = 3 | | | | |
|---|---|---|---|---|---|
| Sample | 0 min | 5 min | 15 min | 30 min | 45 min |
| SAMPLE 9-D (microcapsule) | 0 | 34 (3) | 83 (5) | 97 (2) | 97 (1) |
| SAMPLE 33 | 0 | 37 (1) | 84 (3) | 96 (2) | 95 (1) |
| SAMPLE 37 | 0 | 44 (3) | 90 (5) | 97 (0) | 96 (1) |
| SAMPLE 39 | 0 | 49 (2) | 93 (4) | 97 (1) | 96 (1) |

The dissolution characteristics of the formulated products are similar to that of the microcapsules with a small increase in dissolution rate recorded overall.

Figure 20:
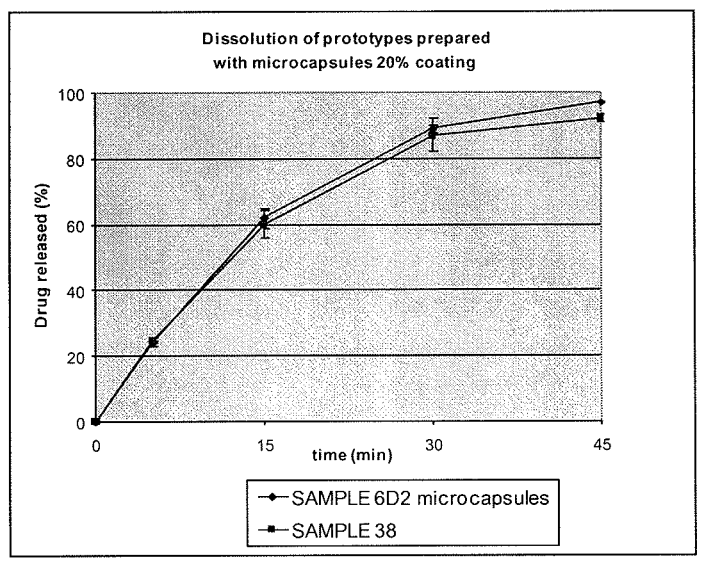
FIG. 20: Dissolution rate of fexofenadine from formulated and plain microcapsules with 20% average Ethylcellulose weight.

The dissolution of formulated product containing microcapsules with an average EC weight of 20% is carried out using pH 6.8 JP 2° nd fluid. These results are compared to unformulated microcapsules. These results are summarized in Table 31 below and also are presented as a graph in FIG. 20.

TABLE 31

Percent Fexofenadine Release from Microcapsules and two Fexofenadine microcapsules/granulates mixtures using Microcapsules with an Average EC Weight of 20%

| Sample | Drug release % (SD) n = 3 | | | | |
|---|---|---|---|---|---|
| | 0 min | 5 min | 15 min | 30 min | 45 min |
| SAMPLE 6-D2 (microcapsule) | 0 | 24 (1) | 62 (3) | 89 (1) | 97 (0) |
| SAMPLE 38 | 0 | 25 (1) | 60 (4) | 87 (5) | 92 (1) |

Figure 21:
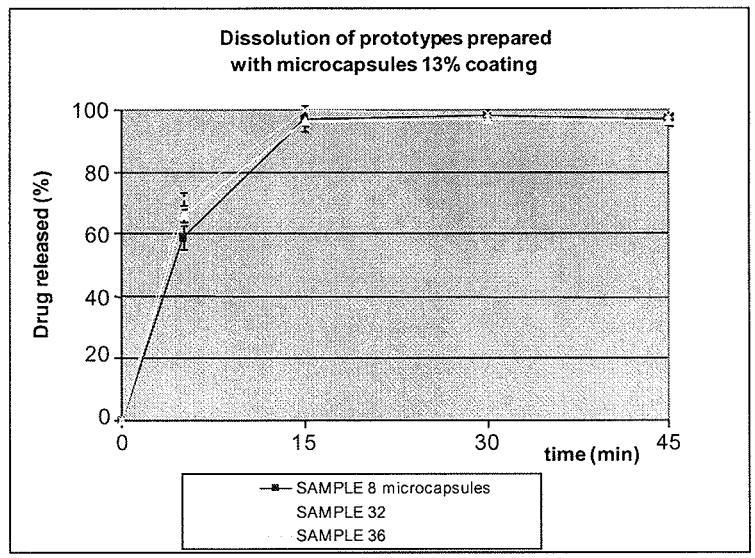
FIG. 21: Dissolution profiles at pH 6.8 (2° fluid JP) of microcapsules 13% ethylcellulose (SAMPLE 8) and the corresponding prototypes SAMPLE 36-SAMPLE 32.
Figure 22:
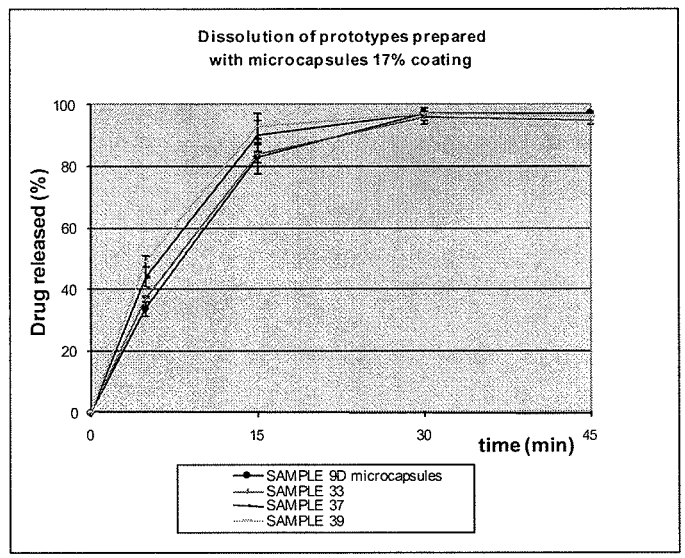
FIG. 22: Dissolution profiles at pH 6.8 (2° fluid JP) of microcapsules 17% Ethylcellulose (SAMPLE 9-D) and the corresponding prototypes SAMPLE 37-SAMPLE 39-SAMPLE 33.
Figure 23:
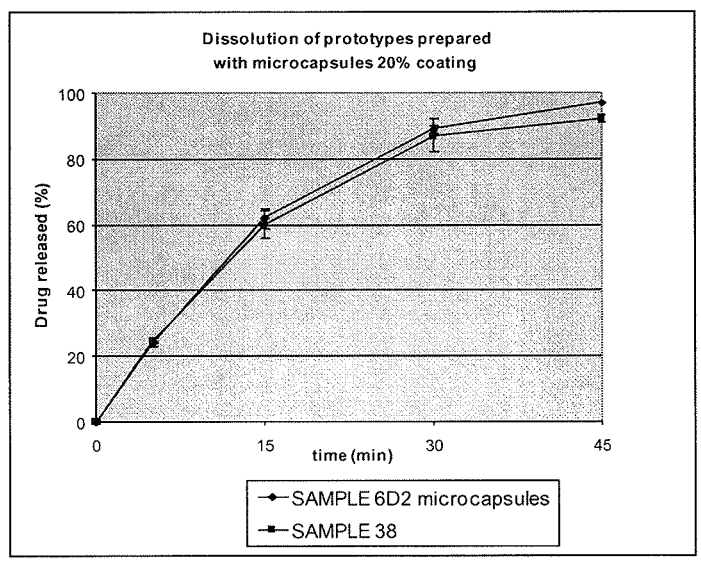
FIG. 23: Dissolution profiles at pH 6.8 (2° fluid JP) of microcapsules 20% Ethylcellulose (SAMPLE 6-D2) and the corresponding prototype SAMPLE 38.
Figure 24:
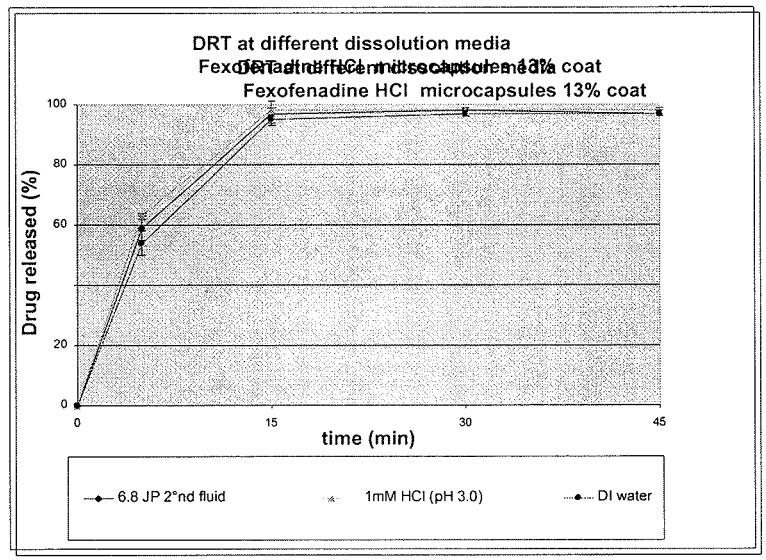
FIG. 24: Dissolution rate of 13% average coating weight microcapsules (SAMPLE 8) in various dissolution media.
Figure 25:
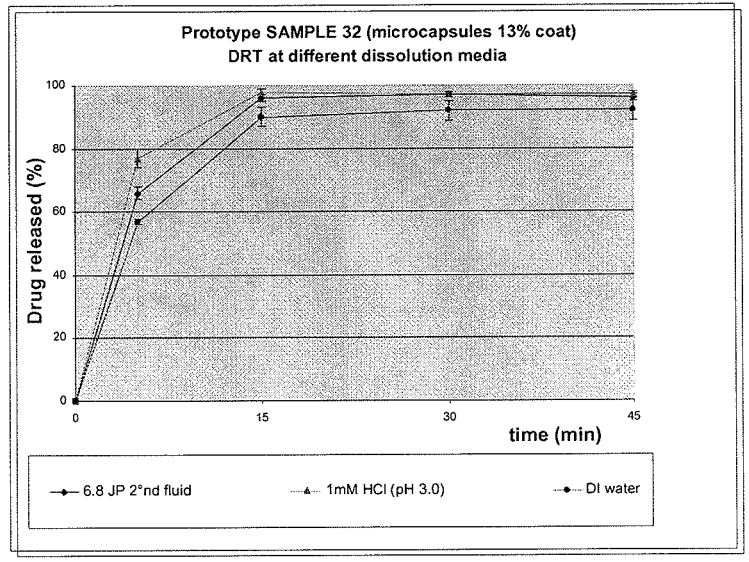
FIG. 25: Dissolution rates of formulated product containing 13% average ethylcellulose weight microcapsules (SAMPLE 32) in various dissolution media.
Figure 26:
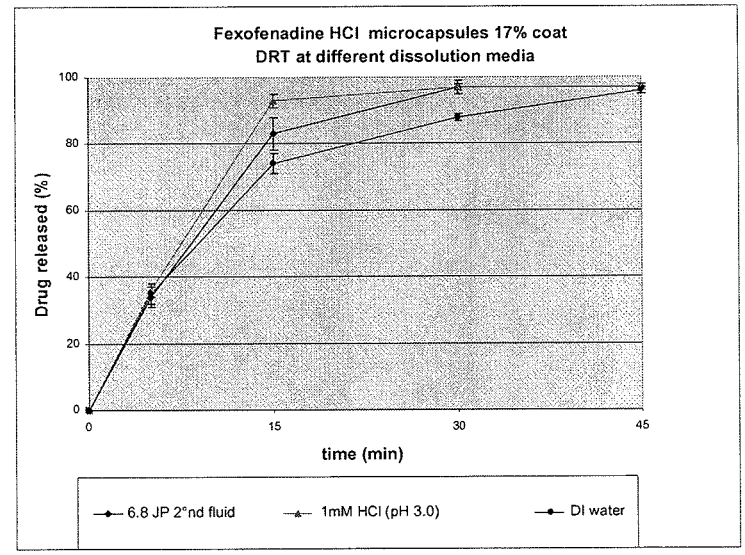
FIG. 26: Dissolution rates of 17% average coating weight microcapsules (SAMPLE 9-D) in various dissolution media.
Figure 27:
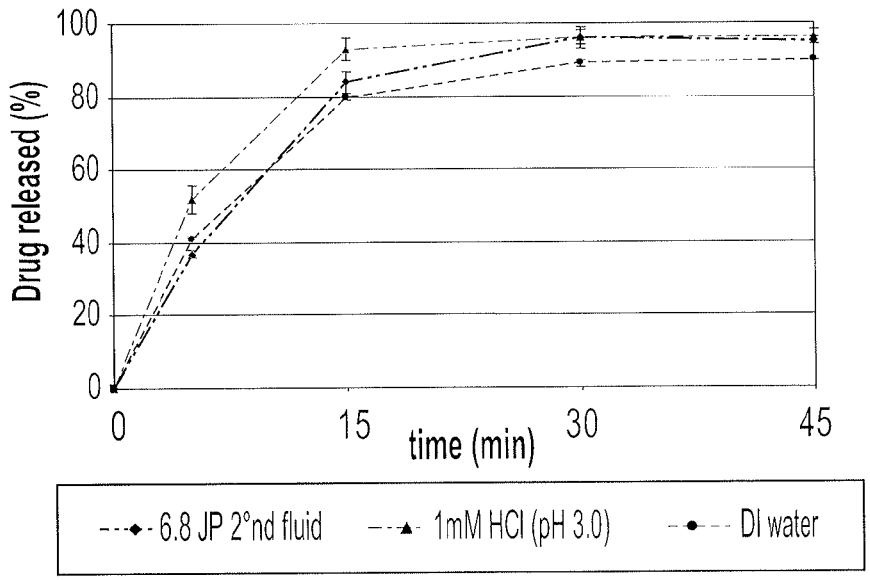
FIG. 27: Dissolution rates of formulated product containing 17% average ethylcellulose weight microcapsules (SAMPLE 33) in various dissolution media.

For each coating level, the dissolution rate of the formulated microcapsule prototypes is similar to the dissolution rate of microcapsules alone (see FIGS. 21-23). The selected inactive ingredient(s) did not seem to affect the dissolution profile of the microcapsules.

The dissolution rate for formulated product batches is also carried out using microcapsules with 13% and 17% coatings and tested with 1 mM HCl; and DI water. The results are reported in the hereunder Tables which also include the values for dissolution in pH 6.8 JP 2° nd fluid as reported above, and are represented graphically in FIGS. 24-27.

TABLE 32

Dissolution Rate of 13% Average Ethylcellulose Weight Microcapsules (SAMPLE 8) in Various Dissolution Media

| Dissolution Medium | Drug release % (SD) n = 3 | | | | |
|---|---|---|---|---|---|
| | 0 min | 5 min | 15 min | 30 min | 45 min |
| 6.8 JP 2°nd | 0 | 59 (4) | 97 (4) | 98 (1) | 97 (1) |
| 1 mM HCl (pH 3.0) | 0 | 63 (1) | 98 (1) | 98 (0) | 98 (1) |
| DI water | 0 | 54 (4) | 95 (1) | 97 (1) | 97 (1) |

TABLE 33

Dissolution Rate of Fexofenadine microcapsules/granulates mixtures Containing 13% Average Ethylcellulose Weight Microcapsules (SAMPLE 32) in Various Dissolution Media

| Dissolution Medium | Drug release % (SD) n = 3 | | | | |
|---|---|---|---|---|---|
| | 0 min | 5 min | 15 min | 30 min | 45 min |
| 6.8 JP 2°nd fluid | 0 | 66 (2) | 96 (1) | 97 (1) | 96 (1) |
| 1 mM HCl (pH 3.0) | 0 | 77 (3) | 98 (1) | 97 (1) | 97 (1) |
| DI water | 0 | 57 (1) | 90 (3) | 92 (3) | 92 (3) |

TABLE 34

Dissolution Rates of 17% Average Ethylcellulose Weight Microcapsules (SAMPLE 9-D) in Various Dissolution Media

| Dissolution Medium | Drug release % (SD) n = 3 | | | | |
|---|---|---|---|---|---|
| | 0 min | 5 min | 15 min | 30 min | 45 min |
| 6.8 JP 2°nd fluid | 0 | 34 (3) | 83 (5) | 97 (2) | 97 (1) |
| 1 mM HCl (pH 3.0) | 0 | 36 (2) | 93 (2) | 97 (1) | 97 (1) |
| DI water | 0 | 35 (3) | 74 (3) | 88 (1) | 96 (1) |

Dissolution rates of sachet prototype SAMPLE 33, containing microcapsule SAMPLE 9-D (17% average ethylcellulose weight) are reported below in Table 35.

TABLE 35

Dissolution Rates of Fexofenadine microcapsules/granulates mixtures Containing 17% Average Ethylcellulose Weight Microcapsules (SAMPLE 33) in Various Dissolution Media

| Dissolution Medium | Drug release % (SD) n = 3 | | | | |
|---|---|---|---|---|---|
| | 0 min | 5 min | 15 min | 30 min | 45 min |
| 6.8 JP 2°nd fluid | 0 | 37 (1) | 84 (3) | 96 (2) | 95 (1) |
| 1 mM HCl (pH 3.0) | 0 | 52 (4) | 93 (3) | 96 (3) | 96 (2) |
| DI water | 0 | 41 (1) | 80 (1) | 89 (1) | 90 (0) |

The dissolution rates of the formulated prototypes are similar to the dissolution profile of the corresponding microcapsules. The inactive ingredient(s) that is used do not appear to affect the dissolution profile of the microcapsules.

2.3.2 Second Set of Examples of Formulated Fexofenadine Microcapsules Blended with and SGX Granulates)

A second series of fexofenadine products is prepared (Table 36). These compositions are prepared based on the following criteria: 1) prototypes are formulated using microcapsules with 13% or 15% coating; 2) β-cyclodextrin is not used; 3) a unique amount of flavour, banana or strawberry, is used for all the prototypes; 4) the flavour is introduced in the formulation mixed with the SG granulate and with a small amount of silicon dioxide.

TABLE 36

Composition of Fexofenadine Prototypes-Second Set

| | SAMPLE 40 | SAMPLE 41 | SAMPLE 42 | SAMPLE 43 |
|---|---|---|---|---|
| Fexofenadine microcapsule 13% | 36.0 | | 36.0 | |
| Fexofenadine microcapsule 15% | | 37.0 | | 37.0 |
| SG granulate + banana flavour + silicon dioxide | 150.0 | 150.0 | | |
| SG granulate + strawberry flavour + silicon dioxide | | | 150.0 | 150.0 |
| SGX granulate | 400.0 | 400.0 | 400.0 | 400.0 |
| Total (mg) | 586.0 | 587.0 | 586.0 | 587.0 |

Fexofenadine is released with a fast mechanism (i.e., ≥80% release at 15 min.) (Table 37).

TABLE 37

"In vitro" dissolution values of Fexofenadine at pH 6.8 2° Fluid JP, from Prototypes Second Set.

| | Drug release % (SD) n = 3 | | | | |
|---|---|---|---|---|---|
| | 0 min | 5 min | 15 min | 30 min | 45 min |
| SAMPLE 40 (13%) | 0 | 65 (2) | 95 (4) | 96 (3) | 96 (3) |
| SAMPLE 41 (15%) | 0 | 60 (2) | 97 (3) | 97 (3) | 97 3) |

2.3.3 Third Set of Examples of Formulated Fexofenadine Microcapsules Blended with SGX Granulates Additional prototypes are prepared as follows. Fexofenadine microcapsules are combined with SGX granules, and the amount of xanthan gum is reduced from 1.5 to 1.1% w/w in the SGX granulate so that the concentration of the xanthan gum remains equal to 1.0% w/w.

TABLE 38

Composition of Third Set Fexofenadine Prototypes

|  | Test Drug T1 | | Test Drug T2 | |
| --- | --- | --- | --- | --- |
|  | Mg | % | mg | % |
| Fexofenadine Microcapsules | 36.00 | 6.15 | 37.0 | 6.30 |
| Granulate Sucrose/Xanthan Gum (1.1% w/w) | 549.10 | 93.70 | 549.10 | 93.55 |
| Silicon Dioxide | 0.60 | 0.10 | 0.60 | 0.10 |
| Strawberry flavour | 0.30 | 0.05 | 0.30 | 0.05 |
| Total | 586.00 | 100.00 | 587.00 | 100.00 |

2.4 Preparation of Examples of Fexofenadine Granules 2.4.1 First Set Granulation Fexofenadine Microcaps with Sucrose and Xanthan Gum One part of fexofenadine microcapsules (15% by weight of Ethylcellulose) is granulated together with 6 parts of sucrose powder into a fluid bed fitted with a top spray (Glatt GPCG3). The binding solution that is consisted of an aqueous solution of sucrose (15% w/w) and xanthan gum (0.5% w/w) is sprayed at room temperature. At the end of the granulation process the granules are dried, then the dried granules are removed from the fluid bed and sieved. The granules are characterized for particle size distribution (vibrating sieve test), release profile of fexofenadine (dissolution test in USP apparatus II, using 900 mL of pH 6.8 buffer, Japan $2^{nd}$, at 37° C. and paddle speed of 50 rpm), active ingredient content uniformity and appearance (optical microscopy test).

Content uniformity tests show that fexofenadine microcapsules are homogeneously distributed into granules: measured average content (n=15) and relevant % RSD are respectively 111 mg/g (theoretical adjusted according microcapsules assay: 114 mg/g) and 3.2%. Optical microscopy appears to show that the granulation process results in the embedding of microcapsules in sucrose granules or the adhesion of microcapsules onto sucrose granules.

TABLE 39

Size distribution of granules as obtained and of corresponding microcapsules

| Sieve opening μm | Granules Amount retained % w/w | Starting microcapsules Amount retained % w/w |
| --- | --- | --- |
| 600 | 0.0 (0.0) | NA |
| 500 | 2.7 (0.2) | NA |
| 355 | 21.5 (1.1) | 0.0 (0.0) |
| 250 | 38.9 (1.0) | 0.1 (0.1) |
| 212 | 16.3 (0.3) | 0.2 (0.0) |
| 180 | 8.7 (0.8) | 0.3 (0.1) |
| 125 | 7.8 (0.6) | 1.1 (0.3) |
| 90 | 2.5 (0.2) | 26.1 (1.5) |
| Bottom | 1.7 (0.3) | 72.3 (1.7) |

TABLE 40

Amount of fexofenadine released from granules and from the corresponding microcapsules in pH 6.8 buffer (Japan $2^{nd}$ fluid).

| Time (min) | Microcapsules release % of theoretical (n = 6) | Granules release SAMPLE 44 % of theoretical (n = 6) |
| --- | --- | --- |
| 5 | 69 (3) | 64 (1) |
| 15 | 97 (1) | 93 (4) |
| 30 | 99 (1) | 94 (2) |
| 45 | 98 (1) | 93 (3) |

2.4.2 Second Set of Examples of Granulation Fexofenadine Microcaps with Sucrose and Xanthan Gum One part of fexofenadine microcapsules (15% by weight of ethylcellulose) is granulated together with 14 parts of sucrose powder into fluid bed fitted with top spray (Glatt GPCG3). The binding solution that is consisted of an aqueous solution of sucrose (15% w/w) and xanthan gum (0.5% w/w) is sprayed at room temperature. At the end of the granulation process the granules are dried then the dried granules are removed from the fluid bed and sieved.

The granules that are collected are characterized for particle size distribution (vibrating sieve test), the release profile of fexofenadine (dissolution test in USP apparatus II, using 900 mL of pH 6.8 buffer, Japan $2^{nd}$, at 37° C. and paddle speed of 50 rpm), active ingredient content uniformity and appearance (optical microscopy test).

Content uniformity tests appear to show that the granules are homogeneously distributed: average content and % RSD respectively 53.5 mg/g (theoretical value adjusted according microcapsules assay: 54.5 mg/g) and 2.8%.

Granules appearance (optical microscopy) is close to that of granules prepared in the first set using the same batch of microcapsules.

Granulation success is confirmed also by size distribution data (vibrating sieve test): aggregation of sucrose and microcapsules lead to significant particle size increase (Table 41). Moreover granules size distribution is comparable with that of the granules produced in the first set (microcapsules/sucrose weight ratio 1:6)

TABLE 41

Size distribution of granules as obtained in first set and of corresponding microcapsules

| Sieve opening μm | Granules Amount retained % w/w | Starting microcapsules Amount retained % w/w |
| --- | --- | --- |
| 600 | 0.0 (0.0) | NA |
| 500 | 1.2 (0.2) | NA |
| 355 | 13.7 (0.8) | 0.0 (0.0) |
| 250 | 41.1 (1.0) | 0.1 (0.1) |
| 212 | 20.3 (0.1) | 0.2 (0.0) |
| 180 | 10.9 (0.8) | 0.3 (0.1) |
| 125 | 9.2 (0.5) | 1.1 (0.3) |
| 90 | 2.1 (0.2) | 26.1 (1.5) |
| bottom | 1.5 (0.3) | 72.3 (1.7) |

TABLE 42

Amount of fexofenadine released from granules and from corresponding microcapsules in pH 6.8 buffer (Japan 2$^{nd}$ fluid).

| Time (min) | Microcapsules release % of theoretical (n = 6) | Granules release % of theoretical (n = 6) |
|---|---|---|
| 5 | 69 (6) | 64 (1) |
| 15 | 97 (4) | 93 (4) |
| 30 | 99 (4) | 94 (2) |
| 45 | 99 (4) | 93 (3) |

2.4.3 Third Set of Examples of Granulation Fexofenadine Microcaps with Sucrose and Xanthan Gum A homogenous final mixture is obtained by granulating fexofenadine microcapsules with a portion of the excipients, then subsequently blended with the remaining inactive ingredients in a granulated form. Mixtures with similar particle sizes are mixed in a 1:1 w/w ratio. This co-granulation process is carried out in a lab-scale top-spray fluid bed (GPCG 3, 7 inches). Microcapsules are combined in ratio of 1:6 w/w with sucrose and granulated using a binder solution of sucrose aqueous solution (5% w/w) containing 0.5% w/w of xanthan gum.

One batch of granulates, SAMPLE 45, is made by combining microcapsules in a ratio of 1:6 w/w with sucrose using a binder solution of sucrose aqueous solution (5% w/w) in absence of xanthan gum. The addition of the xanthan gum and the concurrent increase of the amount of sucrose in the binder solution improves the process of the co-granulation of microcapsules with sucrose. Table 43 lists the PSD of the resulting granulates. and drug assay as f(PSD):

TABLE 43

PSD of the co-granulate manufactured at lab scale:

| | >600 µm | 500 µm | 355 µm | 250 µm | 212 µm | 180 µm | 125 µm | 90 µm | <90 µm |
|---|---|---|---|---|---|---|---|---|---|
| SAMPLE 45 | 0.2 | 1.3 | 4.7 | 19.5 | 19.4 | 15.1 | 22.9 | 9.0 | 7.9 |
| SAMPLE 46 | 0.3 | 4.4 | 24.7 | 38.9 | 14.9 | 7.5 | 6.3 | 1.8 | 1.1 |
| U9A333 | 0.0 | 0.6 | 6.3 | 24.6 | 20.4 | 14.2 | 20.5 | 7.7 | 5.8 |
| SAMPLE 44 | 0.0 | 2.7 | 21.5 | 38.9 | 16.3 | 8.7 | 7.8 | 2.5 | 1.7 |
| SAMPLE 47 | 0.0 | 1.8 | 10.1 | 26.7 | 16.2 | 12.2 | 18.2 | 6.6 | 8.2 |
| SAMPLE 48 | 3.9 | 6.9 | 26.3 | 36.8 | 13.3 | 6.3 | 5.3 | 0.9 | 0.2 |
| SAMPLE 49 | 4.1 | 7.3 | 31.0 | 38.8 | 11.1 | 4.0 | 2.5 | 0.4 | 0.5 |
| SAMPLE 50 | 3.9 | 5.5 | 23.9 | 38.8 | 15.3 | 7.1 | 4.7 | 0.7 | 0.1 |

The theoretical assay value is always about 100 mg/g for all the manufactured granulates. Microscopic observation shows that the fine fraction (<125 micron) is richer in microcapsules when compared with the larger fractions.

"In vitro" dissolution values are given hereunder for some of the manufactured granulates

TABLE 44

The dissolution values and drug assays for lab-scale granulates

| | pH 6.8 2nd fluid JP | | | | |
|---|---|---|---|---|---|
| Batch | 5 min | 15 min | 30 min | 45 min | CUT (n = 15) |
| SAMPLE 46 | 50 ± 3 | 89 ± 2 | 95 ± 1 | 94 ± 1 | 113.5 (RSD 2.6) |
| SAMPLE 44 | 64 ± 1 | 93 ± 4 | 94 ± 2 | 93 ± 3 | 111.0 (RSD 3.2) |
| SAMPLE 48 | 44 ± 2 | 79 ± 2 | 93 ± 2 | 95 ± 2 | 108.7 (RSD 2.4) |
| SAMPLE 49 | 57 ± 2 | 96 ± 1 | 99 ± 1 | 99 ± 2 | 112.5 (RSD 0.7) |

In order to control the fraction of small particles the granulation process parameters and the amount of binder solution may be adjusted.

Figure 28:
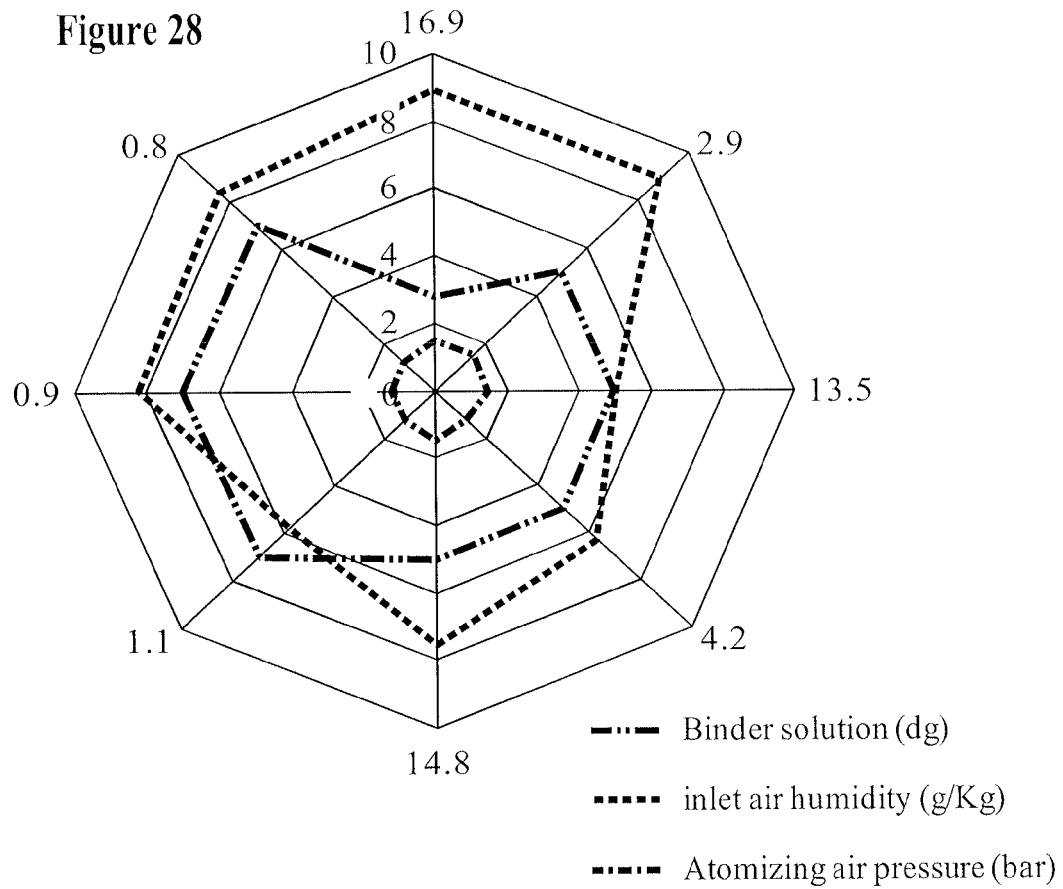
FIG. 28: The radar graph describes the influence of the process parameters onto the formation of small particles.

The graph displayed in FIG. 28 correlates three process parameters: the amount of the binder solution sprayed onto the powder, the inlet air humidity, and the atomizing air pressure. Granulates with a lower percentage of the fine fraction (values are reported on the octagon angles in the Figure) are generated using the lowest atomizing pressure, highest amount of binder solution, and the appropriate inlet air humidity. The co-granulate that is produced has a fine fraction <3% and a drug content with a RSD (relative standard deviation) of less than 3.0%.

2.4.4 Fourth Set of Examples of Granulation Fexofenadine Microcaps with Sucrose and Xanthan Gum. Industrial scale The wetted microcapsules are co-granulated with the sucrose fine powder using the same binder solution used during the lab-scale studies. In particular, 14.70 kg of wet microcapsules are granulated with 102.90 kg of sucrose fine powder (ratio 1:7), using 29.40 kg of binder solution. The obtained granulate is sieved through a 840 µm stainless steel sieve. The sieved product is placed in a double PE bag in plastic drums.

TABLE 45

Theoretical composition of this fexofenadine co-granulates SAMPLE 52.

| components | % w/w |
|---|---|
| Fexofenadine | 9.93 |
| Ethylcellulose | 1.75 |
| Sodium Docusate | 0.07 |
| Silicon Dioxide | 0.27 |
| Sucrose | 87.86 |
| Xanthan Gum | 0.12 |

The obtained co-granulate is characterized in terms of PSD, drug assay as f(PSD), water content (0.13%) and "in vitro" dissolution values in pH 6.8 2$^{nd}$ fluid JP. Data are reported in the following tables.

TABLE 46

PSD of the co-granulate manufactured at industrial scale:

| | >600 μm | 500 μm | 355 μm | 250 μm | 212 μm | 180 μm | 125 μm | 90 μm | <90 μm |
|---|---|---|---|---|---|---|---|---|---|
| SAMPLE 51 | 21.9 | 17.5 | 32.9 | 21.7 | 3.9 | 1.3 | 0.9 | 0.0 | 0.0 |
| SAMPLE 52 | 4.6 | 6.5 | 19.4 | 29.5 | 15.5 | 9.5 | 10.9 | 2.7 | 1.4 |

TABLE 47

"In vitro" dissolution values in buffer pH 6.8 $2^{nd}$ fluid JP and assay (n = 3).

| | | pH 6.8 2nd fluid JP | | | | Assay | |
|---|---|---|---|---|---|---|---|
| Sample | Core | 5 min | 15 min | 30 min | 45 min | (mg/g) | RSD % |
| SAMPLE 52 | SAMPLE 18 | 55 ± 3 | 88 ± 4 | 91 ± 4 | 91 ± 4 | 98.6 | 3.9 |

The amount of the fine particles is low. The RSD is between 1.8% and 6.0%.

2.4.5 Preparation of Sucrose and Xanthan Granulates

Sucrose granules with a PSD similar to that which is obtained with the co-granulate are prepared. This scale up process is performed directly onto the industrial top-spray fluid bed Glatt FB500, 500 L. The process is carried out in a single step: the xanthan gum is directly granulated with the sucrose by spraying the same binder solution used for the co-granulation process, however the ethanol is eliminated.

In particular, 147.0 kg of sucrose fine powder and 3.0 kg of xanthan gum are granulated with 20.0 kg of binder solution. At the end of the granulation process the product is sieved through a 840 μm stainless steel sieve and 149.1 kg of granulate is obtained (process yield 97.4%).

TABLE 48

Binder solution and sucrose/xanthan gum granulate SAMPLE 53 theoretical composition.

| | components | % w/w | Kg | % composition SAMPLE 53 |
|---|---|---|---|---|
| Binder solution | Sucrose | 15.0 | 3.0 | 2.0 |
| | Xanthan Gum | 0.5 | 0.1 | 0.1 |
| | Deionized Water | 84.5 | 16.9 | — |
| Powder | Sucrose fine powder | 88.0 | 147.0 | 96.0 |
| | Xanthan Gum | 2.0 | 3.0 | 1.9 |

The PSD and water content (0.48%) of the resulting granulates are characterized.

TABLE 49

Particle Size Analysis SAMPLE 53 and SAMPLE 54.

| Sieve (μm) | SAMPLE 53 (%) | SAMPLE 54 (%) |
|---|---|---|
| >600 | 8.6 | 5.7 |
| 500 | 9.4 | 9.9 |
| 355 | 23.5 | 25.3 |
| 250 | 30.2 | 31.8 |
| 212 | 11.2 | 11.2 |
| 180 | 7.1 | 5.9 |
| 125 | 6.7 | 6.3 |
| 90 | 1.7 | 1.7 |
| <90 | 1.3 | 2.2 |

The two granulates are prepared applying the same process parameters and resulted in compositions with similar PSD compared to the co-granulate (this is an important requirement in order to confirm that the subsequent mixing step can be successfully carried out).

2.5 Blending of Fexofenadine Granules and Sucrose Granules

The two previous batches of co-granulates and sucrose granulates are mixed with two batches of sugar-based placebo granules having a very similar PSD, at a 1:1 w/w ratio with batch sizes of about 200 kg. The combination of SAMPLE 51 and placebo SAMPLE 55 is designated as SAMPLE 56 after mixing.

TABLE 50

PSD of mixture Batch number SAMPLE 56 (SAMPLE 51 (co-granulates) and SAMPLE 55 (sucrose granulates):

| | >600 μm | 500 μm | 355 μm | 250 μm | 212 μm | 180 μm | 125 μm | 90 μm | <90 μm |
|---|---|---|---|---|---|---|---|---|---|
| SAMPLE 51 | 21.9 | 17.5 | 32.9 | 21.7 | 3.9 | 1.3 | 0.9 | 0.0 | 0.0 |
| SAMPLE 55 | 18.7 | 16.2 | 30.9 | 23.1 | 5.3 | 2.1 | 1.9 | 0.7 | 1.4 |

TABLE 51

PSD of Mixture Batch number SAMPLE 57 (SAMPLE 52 (co-granulates) and SAMPLE 53 (sucrose granulates):

|  | >600 μm | 500 μm | 355 μm | 250 μm | 212 μm | 180 μm | 125 μm | 90 μm | <90 μm |
|---|---|---|---|---|---|---|---|---|---|
| SAMPLE 52 | 4.6 | 6.5 | 19.4 | 29.5 | 15.5 | 9.5 | 10.9 | 2.7 | 1.4 |
| SAMPLE 53 | 8.6 | 9.4 | 23.5 | 30.2 | 11.2 | 7.1 | 6.7 | 1.7 | 1.3 |

The tables below describe the composition of the batches.

TABLE 51

The theoretical composition of the batches.

| components | SAMPLE 56, SAMPLE 57 (%) |
|---|---|
| Fexofenadine | 5.00 |
| Ethylcellulose | 0.88 |
| Sodium Docusate | 0.04 |
| Silicon Dioxide | 0.22 |
| Sucrose | 92.75 |
| Xanthan Gum | 1.06 |
| Strawberry flavour | 0.05 |

TABLE 53

The drug assay and RSD %:

| batch | Drug assay (mg/g), n = 3 | Theoretical assay (mg/g) | RSD % |
|---|---|---|---|
| SAMPLE 56 | 48.1 | 50.0 | 5.6 |
| SAMPLE 57 | 49.0 | 50.0 | 3.9 |

The blend homogeneity (n=10) of mixture SAMPLE 57 is: first assay: 50.5 mg/g (RSD 5.1%); second assay: 50.7 mg/g (RSD 5.5%). The performed trials indicate that the average assay is close to the theoretical value (50 mg/g).

The dissolution performance of fexofenadine bulk mix (SAMPLE 57) in buffer pH 6.8 $2^{nd}$ fluid JP (compared with the respective co-granulate (SAMPLE 52) (n=6)) and in pH 3.0 are reported below

TABLE 54

The dissolution profiles of fexofenadine bulk mix (SAMPLE 57) and the co-granulate (SAMPLE 52) (n = 6) in buffer pH 6.8 $2^{nd}$ fluid JP

| Time (min) | 5 | 10 | 15 | 30 | 45 | 60 |
|---|---|---|---|---|---|---|
| SAMPLE 52 | 55 ± 3 | 82 ± 5 | 88 ± 4 | 91 ± 4 | 91 ± 4 | 92 ± 5 |
| SAMPLE 57 | 62 ± 2 | 86 ± 7 | 90 ± 5 | 92 ± 4 | 91 ± 4 | 91 ± 4 |

The mixing process shows a slight increase in the dissolution rate during the first five minutes, this effect could be possibly related to a mechanical stress that is involved during the mix.

TABLE 55

The dissolution profiles of fexofenadine bulk mix (SAMPLE 57) in pH 3.0

| Time (min) | 5 | 10 | 15 | 30 | 45 | 60 |
|---|---|---|---|---|---|---|
| % fexofenadine released | 63 ± 10 | 84 ± 10 | 92 ± 9 | 95 ± 8 | 94 ± 8 | 94 ± 8 |

The dissolution data for SAMPLE 57 confirm the fast release.

2.6 Sachet Filling

Strength 15 mg are produced corresponding to 300 mg of mixture. The filling machine produces 2 sachets in line (7.0 mm×5.8 mm). The maximum productivity is 170 sachets/min (speed 85 rpm). The material that is used for the preparation of the sachets is 3LAMINET/M AL12960 (PET 12 μm, Aluminium 9 μm, antistatic PE 60 μm).

A feeding screw is present between the bag and the feeding hopper along with a sensor to detect the quantity of powder in order to keep the amount of mixture in the hopper consistent (when the volume of the mixture is decreased, the screw feeds the hopper). The hopper is bipartite having a left and right filling system, each side is equipped with a single dosing screw. Inside there are two stirring systems (left and right) that maintain the mix under gentle agitation during the process.

Sachet filling trials are carried out starting from a mixture that is prepared with a co-granulate with different levels of fine particles and PSD In some cases the theoretical assay value of the mixture is lower and therefore the target strength of each drug content can be variable.

Sachet SAMPLE 58 is produced by using the bulk mix SAMPLE 57 (50.0 mg/g RSD 5.6%). The PSD of the bulk mix SAMPLE 57 is given in Table 51. Parameters of the machine are set as given in the Table below

TABLE 56

Filling machine process parameters.

| Parameters | values |
|---|---|
| Machine speed | 85 rpm |
| Flow stopper | 1.6 mm |
| Weight control on line in exit | 54.5 g ± 0.7 g |

TABLE 57

Limits of acceptance SAMPLE 58.

| Tests | Limits of acceptance |
|---|---|
| Weight | 285-315 mg |
| Mass content | T1 = 3.0% (±9 mg) |
|  | T2 = 5.0% (±15 mg) |

TABLE 58

Assay results SAMPLE 58.

| | Shipping case | | | | | |
|---|---|---|---|---|---|---|
| | 2 | | 4 | | 6 | |
| sample | weight (mg) | Assay (mg/sachet) | weight (mg) | Assay (mg/sachet) | weight (mg) | Assay (mg/sachet) |
| 1 | 302.1 | 15.2 | 295.3 | 14.4 | 298.2 | 14.4 |
| 2 | 310.8 | 15.5 | 297.3 | 14.4 | 296.2 | 14.2 |
| 3 | 310.7 | 15.4 | 309.9 | 15.1 | 300.1 | 14.0 |
| 4 | 314.8 | 16.1 | 307.3 | 15.1 | 300.0 | 14.1 |
| 5 | 316.1 | 15.6 | 302.2 | 14.9 | 304.1 | 14.6 |
| 6 | 298.5 | 15.3 | 322.7 | 15.6 | 291.6 | 14.8 |
| 7 | 313.5 | 16.1 | 306.4 | 14.7 | 290.2 | 14.0 |
| 8 | 310.3 | 15.8 | 294.2 | 14.4 | 298.8 | 14.3 |
| 9 | 305.8 | 15.9 | 307.2 | 15.2 | 297.0 | 14.3 |
| 10 | 304.9 | 15.7 | 307.2 | 14.6 | 297.4 | 14.4 |
| average | 308.8 | 15.7 | 305.0 | 14.8 | 297.4 | 14.3 |
| Sd | 5.7 | 0.3 | 8.4 | 0.4 | 4.1 | 0.3 |
| RSD | 1.8 | 1.9 | 2.8 | 2.7 | 1.4 | 2.1 |
| Recovery % | | 104.7 | | 98.7 | | 95.3 |
| | Mass variation | Content uniformity | Mass variation | Content uniformity | Mass variation | Content uniformity |
| AV | 7.8 | 8.0 | 6.5 | 6.5 | 6.3 | 7.2 |

The results indicate that 300 mg sachet having mass variation between 6.3 and 7.8 and content uniformity between 6.5 and 8.0 are be obtained with the fexofenadine microcapsule co-granulate of the invention.

2.6.2 Sachet Filling with Mixture SAMPLE 57 >125 μm

Bulk mixture SAMPLE 57 >125 micron is prepared from SAMPLE 57 by removing the fine fraction (<125 micron); this is performed by sieving. The PSD data of the mixture is reported in Table 59

TABLE 59

| sieve | SAMPLE 57 > 125 μm |
|---|---|
| >600 | 10.0 |
| 355 | 37.0 |
| 212 | 39.2 |
| 125 | 13.1 |
| <125 | 0.5 |

Sachet filling trials are carried out on the 15 mg dose sachet using this bulk mixture. The batch number of sachets SAMPLE 79 is obtained. The following Table summarizes the results:

TABLE 60

Assay results SAMPLE 79.

| | Shipping case | | | | | |
|---|---|---|---|---|---|---|
| | 2 | | 4 | | 8 | |
| Sample | weight (mg) | Assay (mg/sachet) | weight (mg) | Assay (mg/sachet) | weight (mg) | Assay (mg/sachet) |
| 1 | 318.6 | 14.1 | 316.1 | 13.5 | 303.7 | 13.6 |
| 2 | 319.6 | 14.2 | 294.5 | 13.8 | 307.4 | 13.9 |
| 3 | 308.4 | 13.9 | 310.6 | 13.7 | 306.3 | 13.5 |
| 4 | 319.8 | 14.2 | 305.2 | 13.3 | 305.3 | 13.9 |
| 5 | 319.0 | 14.0 | 302.7 | 14.2 | 306.8 | 14.0 |
| 6 | 313.6 | 14.0 | 301.3 | 13.2 | 306.2 | 13.4 |
| 7 | 317.3 | 14.0 | 312.8 | 13.5 | 304.5 | 13.5 |
| 8 | 319.1 | 14.3 | 298.5 | 13.1 | 314.8 | 13.9 |
| 9 | 309.9 | 13.7 | 310.4 | 13.7 | 313.1 | 13.6 |
| 10 | 325.6 | 14.5 | 303.5 | 12.9 | 302.7 | 13.6 |
| Average | 317.1 | 14.1 | 305.6 | 13.5 | 307.1 | 13.7 |
| Sd | 5.1 | 0.2 | 6.8 | 0.4 | 3.9 | 0.2 |
| RSD | 1.6 | 1.4 | 2.2 | 3.0 | 1.3 | 1.5 |
| Recovery | | 102.2 | | 97.8 | | 99.3 |

TABLE 60-continued

Assay results SAMPLE 79.

| | Shipping case | | | | | |
|---|---|---|---|---|---|---|
| | 2 | | 4 | | 8 | |
| Sample | weight (mg) | Assay (mg/sachet) | weight (mg) | Assay (mg/sachet) | weight (mg) | Assay (mg/sachet) |
| | Mass variation | Content uniformity | Mass variation | Content uniformity | Mass variation | Content uniformity |
| AV | 4.6 | 4.5 | 5.9 | 7.4 | 3.0 | 3.7 |

Good results in term of filling weight are obtained and moreover the assay of the sachet is practically equal to the theoretical value (13.8 mg/g); no segregation phenomena occurs.

2.6.3 Sachet Filling with Mixture SAMPLE 56

Trials are carried out on the 15 mg dose sachet using the bulk mixture SAMPLE 56. The PSD of the bulk mix is reported in Table 61.

TABLE 61

Assay results for sachets with SAMPLE 56

| | Shipping case | | | | | | | |
|---|---|---|---|---|---|---|---|---|
| | 1 | | 2 | | 3 | | 4 | |
| sample | weight (mg) | Assay (mg/sachet) | weight (mg) | Assay (mg/sachet) | weight (mg) | Assay (mg/sachet) | weight (mg) | Assay (mg/sachet) |
| 1 | 315.1 | 15.9 | 315.0 | 16.0 | 313.2 | 16.4 | 303.8 | 16.5 |
| 2 | 310.6 | 16.7 | 324.8 | 16.0 | 314.9 | 16.7 | 319.2 | 15.7 |
| 3 | 318.8 | 16.9 | 316.0 | 16.5 | 316.8 | 16.5 | 303.9 | 16.3 |
| 4 | 315.1 | 16.6 | 319.2 | 16.1 | 309.1 | 16.7 | 305.7 | 16.8 |
| 5 | 313.3 | 16.5 | 323.1 | 17.0 | 309.6 | 16.2 | 302.3 | 16.7 |
| 6 | 313.5 | 16.2 | 314.0 | 14.5 | 316.0 | 15.2 | 300.4 | 15.4 |
| 7 | 312.8 | 15.4 | 312.8 | 15.2 | 317.7 | 15.5 | 339.1 | 15.8 |
| 8 | 315.7 | 15.6 | 314.2 | 15.3 | 314.1 | 15.7 | 298.9 | 14.9 |
| 9 | 313.1 | 16.3 | 317.5 | 14.7 | 315.9 | 14.6 | 300.8 | 15.4 |
| 10 | 312.5 | 15.8 | 316.4 | 15.0 | 314.3 | 14.7 | 298.7 | 14.9 |
| average | 314.1 | 16.2 | 317.3 | 15.6 | 314.2 | 15.8 | 307.3 | 15.8 |
| Sd | 2.1 | 0.5 | 3.8 | 0.8 | 2.7 | 0.8 | 12.0 | 0.7 |
| RSD | 0.7 | 2.9 | 1.2 | 4.9 | 0.9 | 4.8 | 3.9 | 4.2 |
| Rec. % | | 107.9 | | 104.2 | | 105.5 | | 105.6 |

The assay is coherent with the filling weight, always over the theoretical of 300 mg; there is a total absence of segregation phenomena, the assay remains very consistent during all the production and mainly its variability.

2.6.4 Sachet Filling with Industrial Scale Equipment

Further trials are performed using industrial scale equipment; the batch sizes involved are in the range of hundreds kilos for the final bulk mixture and in the order of hundreds of thousands of dosage units.

The fexofenadine co-granulates are prepared starting from wetted microcapsules. Examples of particles size distribution of wetted microcapsules are reported in table 62.

TABLE 62

| Particle size distributions of wetted microcapsules (Sieve methodology) | | |
|---|---|---|
| >355 μm | Between 355 and 125 μm | <125 μm |
| 1.0 | 4.0 | 95.0 |
| 1.0 | 6.0 | 93.0 |
| 0.0 | 2.0 | 98.0 |
| 0.0 | 1.0 | 99.0 |
| 0.0 | 2.0 | 98.0 |
| 1.0 | 2.0 | 97.0 |

The co-granulates are prepared and mixed with granulated ingredients; the three batches that are obtained have the same composition as the batches of Table 51. Trials are carried out on these three batches.

The following table shows data related to Particle Size Distribution, of the mixtures and the Assay and corresponding Standard Deviation of the sachets produced for the 3 batches:

TABLE 63

Particle Size Distribution of the mixtures

| | SAMPLE Number | | |
|---|---|---|---|
| Sieve opening | SAMPLE 59 | SAMPLE 60 | SAMPLE 61 |
| | % retained by each sieve | | |
| >600 μm | 8.2 ± 1.0 | 9.6 ± 0.7 | 13.2 ± 2.1 |
| >355 μm | 49.4 ± 4.9 | 46.8 ± 4.3 | 58.0 ± 0.5 |
| >212 μm | 36.2 ± 2.5 | 37.1 ± 2.6 | 25.4 ± 0.4 |
| >125 μm | 5.2 ± 1.4 | 5.7 ± 2.3 | 2.1 ± 0.8 |
| <125 μm | 1.0 0.7 | 0.7 ± 0.4 | 1.2 ± 0.7 |

Each batch of mixture is used to prepare two batches of sachets, one for each forecasted dosage strength: 15 and 30 mg, where the 30 mg corresponds to 600 mg of filling weight and the 15 mg to the 300 mg.

In detail, each batch of mixture gives rise to the following batches of sachets:
Mixture sample 59→ Sachets 62 (300 mg) and 63(600 mg)
Mixture sample 60→ Sachets 64 (300 mg) and 65 (600 mg)
Mixture sample 61→ Sachets 66 (300 mg) and 67 (600 mg)

The following table shows the experimental values of Assay for each produced batch of sachets:

TABLE 64

Assay of the sachets

| Batch Number | Practical Assay, mg/sachet | Practical Assay, % | SD on practical assay | RSD on practical assay |
|---|---|---|---|---|
| A62 | 14.9 | 99 | 0.4 | 2.7 |
| A63 | 14.8 | 99 | 0.3 | 2.0 |
| A64 | 15.2 | 101 | 0.3 | 2.0 |
| A65 | 30.6 | 102 | 0.5 | 1.6 |
| A66 | 30.3 | 101 | 0.7 | 2.3 |
| A67 | 30.9 | 103 | 0.6 | 1.9 |

Furthermore, sachets containing 600 mg of dry syrup is analysed also in terms of "in vitro" dissolution rate, the dissolution test is carried out at pH=3.0 using n=12 samples. The following table reports the data expressed for % released after 15 minutes, Standard Deviation and Relative Standard Deviation:

TABLE 65

"In vitro" dissolution data 600 mg batches

| | % released | SD | RSD |
|---|---|---|---|
| 63 | 92 | 3 | 3.3 |
| 65 | 93 | 5 | 5.4 |
| 67 | 85 | 3 | 3.5 |

From the above it can be evinced that additional filling weights (600 and 300 mg per unit) and additional dosage strengths (15 mg and 30 mg of fexofenadine HCl per unit) of sachets containing the dry syrup are successfully manufactured.

It will be appreciated that, although specific embodiments of the invention are described herein for purposes of illustration, various modifications may be made without departing from the spirit and scope of the invention.

What is claimed is:

1. A pharmaceutical composition comprising a water suspendable co-granulate of taste-masked immediate release microcapsules, wherein said microcapsules comprise fexofenadine coated with a water-insoluble polymer coating.

2. The pharmaceutical composition of claim 1, wherein said fexofenadine is crystalline fexofenadine.

3. The pharmaceutical composition of claim 1, wherein said fexofenadine is fexofenadine hydrochloride.

4. The pharmaceutical composition of claim 1, wherein said water-insoluble polymer is selected from the group consisting of ethylcellulose, polyvinyl acetate, cellulose acetate, cellulose acetate butyrate, ammonio-methacrylate copolymers and mixtures thereof.

5. The pharmaceutical composition of claim 4, wherein said water-insoluble polymer is ethylcellulose.

6. The pharmaceutical composition of claim 1, wherein the weight of the water insoluble polymer of said microcapsules is from about 2% to about 40%.

7. The pharmaceutical composition of claim 3, wherein said composition releases at least about 60% of said fexofenadine hydrochloride within 15 minutes in pH 6.8 JP 2° nd fluid.

8. The pharmaceutical composition of claim 1, wherein said microcapsules further comprise a surfactant, a glidant and/or an antisticking agent.

9. The pharmaceutical composition of claim 1, further comprising at least one inactive ingredient which is optionally granulated and/or at least one excipient.

10. The pharmaceutical composition of claim 1, wherein said composition is in the form of a tablet, capsule or sachet.

11. The pharmaceutical composition of claim 1, further comprising sodium docusate, and one or more granulated inactive ingredients;
wherein the weight ratio of the co-granulated microcapsules to the granulated inactive ingredients is 1:1.

12. The pharmaceutical composition of claim 1, wherein the co-granulated microcapsules consist of taste-masked immediate release microcapsules, xanthan gum, and sucrose powder granulated together, wherein the weight ratio of the taste-masked immediate release microcapsules to sucrose powder is between 1:6 and 1:7.

13. The pharmaceutical composition of claim 12, wherein the co-granulated microcapsules consist of taste masked immediate release microcapsules, xanthan gum and sucrose, wherein the weight ratio of microcapsules to sucrose powder is about 1:7.

14. The pharmaceutical composition of claim 13, wherein the co-granulated microcapsules have a fine fraction below 125 μm of <5.0%, and a fraction over 600 μm which is <10.0%.

15. The pharmaceutical composition of claim 13, wherein the co-granulated microcapsules have a fine fraction below 125 μm of <5.0%, and a fraction over 600 μm of <5.0%.

16. A process for preparing the pharmaceutical composition of claim 1, wherein the pharmaceutical composition comprises taste-masked immediate release microcapsules comprising fexofenadine coated with a water-insoluble polymer, wherein said process comprises the steps of: (a) dissolving a water-insoluble polymer in an organic solvent; (b) suspending fexofenadine in said organic solvent; (c) applying a coating of said water-insoluble polymer onto said fexofenadine by phase separation; and (d) separating said microcapsules from said organic solvent.

17. The process of claim 16, wherein said fexofenadine is crystalline fexofenadine.

18. The process of claim 16, wherein said fexofenadine is fexofenadine hydrochloride.

19. The process of claim 18, further comprising the step of adding a phase inducer agent to said organic solvent to promote step (c).

20. The process of claim 19, wherein said phase inducer agent is selected from the group consisting of polyethylene, polyisobutylene, butyl rubber, polybutadiene, organosilicon polymers, and paraffin.

21. The process of claim 18, further comprising the following steps: (e) optional wetting of microcapsules; (f) co-granulating the microcapsules with at least one inactive ingredient; (g) separately granulating at least one inactive ingredient; h) mixing of co-granulate obtained in step (f) together with the granulated inactive ingredient obtained in step (g); (i) filling the bulk mixture of step (h) in sachets.

22. The process of claim 21, wherein the inactive ingredient of step f) is sucrose, and wherein the step f) is carried out in the presence of an aqueous binder solution comprising sucrose and xanthan gum.

23. The process of claim 22, wherein the weight ratio of sucrose to xanthan gum in the aqueous binder solution is between 5:0 to 15:0.5.

24. A method for treating an inflammation related condition in an individual comprising administering to an individual in need thereof a pharmaceutical composition comprising taste-masked immediate release microcapsules or taste masked immediate release co-granulated microcapsules, wherein said microcapsules comprise fexofenadine and a water-insoluble polymer coating.

25. The method of claim 24, wherein said fexofenadine is crystalline fexofenadine.

26. The method of claim 24, wherein said fexofenadine is fexofenadine hydrochloride.

27. The method of claim 24, wherein the weight of the water insoluble polymer of said microcapsules is from about 2% to about 40%.

28. The method of claim 24, wherein said inflammation related condition is seasonal allergic rhinitis or chronic idiopathic urticaria.

29. The method of claim 24, wherein said water-insoluble polymer is selected from the group consisting of ethylcellulose, polyvinyl acetate, cellulose acetate, cellulose acetate butyrate, ammonio-methacrylate copolymers and mixtures thereof.

30. The method of claim 24, wherein said composition releases at least about 80% of said fexofenadine hydrochloride within 15 minutes in pH 6.8 JP 2° nd fluid.

31. The method of claims 24-27, 28 or 29 wherein said microcapsules further comprise a surfactant, a glidant and/or an antisticking agent.

32. The method of claim 24 wherein said pharmaceutical composition further comprises at least one inactive ingredient which is optionally granulated and/or at least one excipient.

33. The method of claim 24, wherein said pharmaceutical composition is in the form of a tablet, capsule or sachet.

* * * * *